(12) United States Patent
Arts

(10) Patent No.: US 10,272,134 B2
(45) Date of Patent: *Apr. 30, 2019

(54) AUTOLOGOUS HIV-1 PROTEINS FOR THE TREATMENT OF LATENT HIV-1 INFECTION

(71) Applicant: Case Western Reserve University, Cleveland, OH (US)

(72) Inventor: Eric J. Arts, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/589,283

(22) Filed: May 8, 2017

(65) Prior Publication Data

US 2017/0239325 A1   Aug. 24, 2017

Related U.S. Application Data

(63) Continuation of application No. 14/735,662, filed on Jun. 10, 2015, now Pat. No. 9,642,890.

(60) Provisional application No. 62/010,176, filed on Jun. 10, 2014.

(51) Int. Cl.
*A61K 38/00* (2006.01)
*A61K 38/16* (2006.01)
*A61K 45/06* (2006.01)

(52) U.S. Cl.
CPC ........... *A61K 38/162* (2013.01); *A61K 45/06* (2013.01); *C12N 2740/16033* (2013.01)

(58) Field of Classification Search
CPC .................................................. A61K 38/162
See application file for complete search history.

(56) References Cited

U.S. PATENT DOCUMENTS

| | | | |
|---|---|---|---|
| 2005/0032039 A1* | 2/2005 | Sastry | C07K 14/005 435/5 |
| 2008/0199493 A1* | 8/2008 | Picker | A61K 39/04 424/208.1 |
| 2010/0168004 A1 | 7/2010 | Williams | |
| 2010/0183707 A1 | 7/2010 | Zeichner | |
| 2010/0291067 A1 | 11/2010 | Planelles | |
| 2012/0263782 A1 | 10/2012 | Zeichner | |
| 2013/0096054 A1 | 4/2013 | Kutsch | |
| 2013/0202623 A1 | 8/2013 | Chomont | |
| 2013/0337048 A1 | 12/2013 | Zeichner | |

OTHER PUBLICATIONS

Donahue et al., 2013, Latent HIV-1 can be reactivated by cellular superinfection in a tat-dependent manner, which can lead to the emergence of multidrug-resistant recombinant viruses, Journal of Virology, 87(17): 9620-9632.*
Yu et al., 2009, The HIV envelope but not VSV glycoprotein is capable of mediating HIV latent infection of resting CD4 T cells, PLoS Pathogens, 5(10): 10 pages.*
Donahue et al., 2012, The Viral Protein Tat Can Inhibit the Establishment of HIV-1 Latency, Journal of Virology, 3253-3263.
Marozsan et al., 2003, Development of a yeast-based recombination cloning/system for the analysis of gene products from diverse human immunodeficiency virus type 1 isolates, Journal of Virological Methods, 111: 111-120.
Moore et al., 2005, A Yeast Recombination-Based Cloning System to Produce Chimeric HIV-1 Viruses and Express HIV-1 Genes, Methods in Molecular Biology, 304: Human Retrovirus Protocols: Virology and Molecular Biology (ed. Zhu): 369-385.
Gondois-Rey et al., 2001, Production of HIV-1 by resting memory T lymphocytes, AIDS, 15: 1931-1940.
Bosque et al., 2011, Studies of HIV-1 latency in an ex vivo model that uses primary central memory T cells, Methods, 53(1 ): 54-61.
Shan et al., 2011, Influence of Host Gene Transcription Level and Orientation on HIV-1 Latency in a Primary-Cell Model, Journal of Virology, 85(11 ): 5384-5393.
Siliciano et al., 2013, HIV-1 Eradication Strategies: Design and Assessment, Curr Opinion HIV AIDS, 8(4): 318-325.
Ruelas et al., 2013, An Integrated Overview of HIV-1 Latency, Cell, 155: 519-529.
Sahu et al., 2013, Anti-HIV designer T cells progressively eradicate a latently infected cell line by sequentially inducing HIV reactivation then killing the newly gp120-positive cells, Virology, 446: 268-275.

* cited by examiner

*Primary Examiner* — Amber D Steele
(74) *Attorney, Agent, or Firm* — Tarolli, Sundheim, Covell & Tummino LLP

(57) ABSTRACT

A method of reducing a latent HIV-specific memory-CD4+ T cell pool in a subject includes the steps of: preparing at least one HIV-1 protein coding sequence from a sample obtained from the subject, wherein the sample includes HIV-1 RNA; introducing the at least one HIV-1 protein coding sequence into at least one expression construct using yeast homologous recombination; transfecting a cell with the at least one expression construct, wherein the HIV-1 protein is secreted by the cell and administering a therapeutically effective amount of the secreted HIV-1 protein and a pharmaceutically acceptable carrier to the subject, wherein the secreted HIV-1 protein stimulates latent HIV-specific memory-CD4+ T cells to induce latent HIV-1 replication resulting in HIV-specific memory-CD4+ T cell death in the subject.

27 Claims, 9 Drawing Sheets

Figure 1:
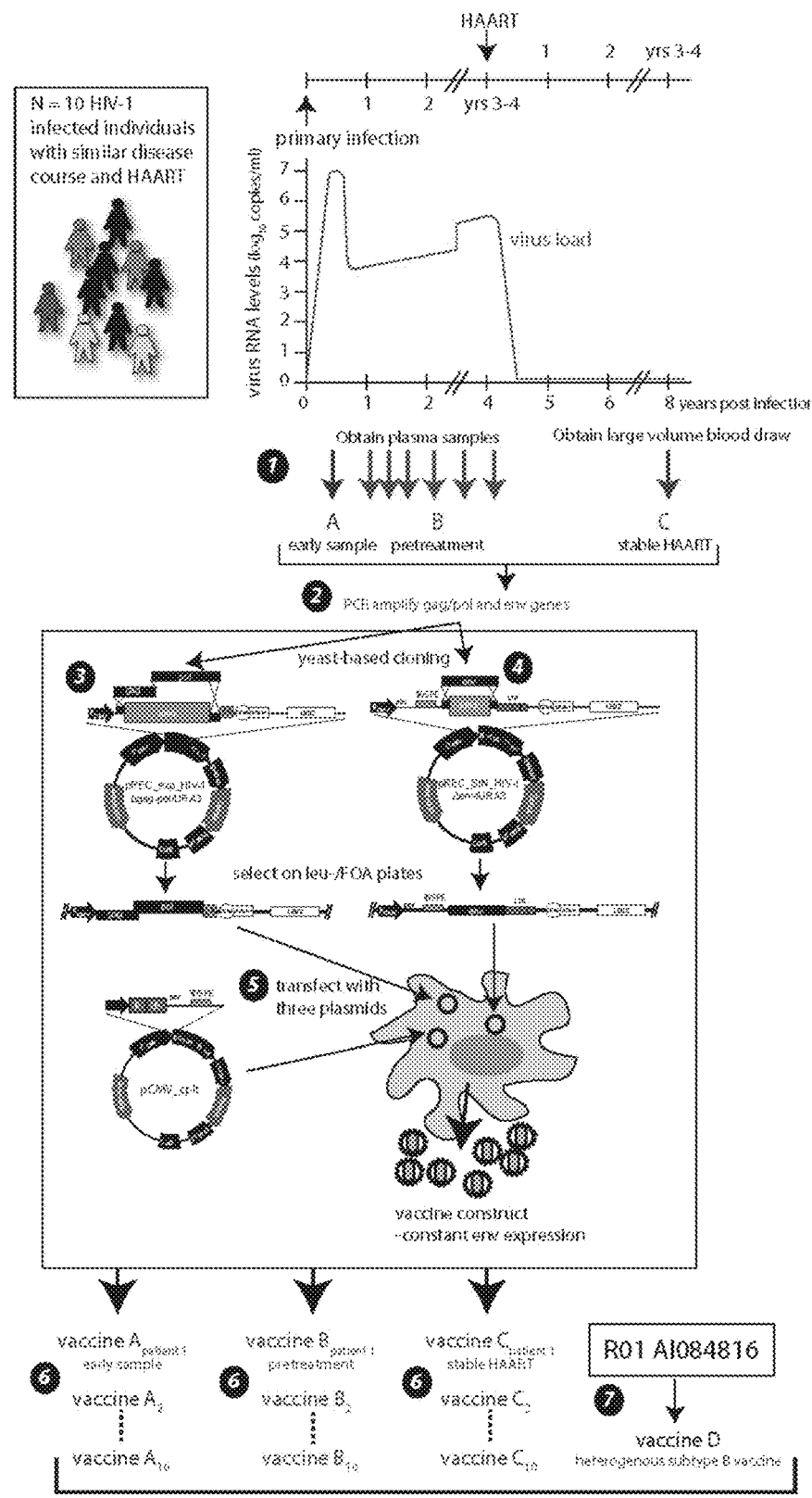
Figure 2:
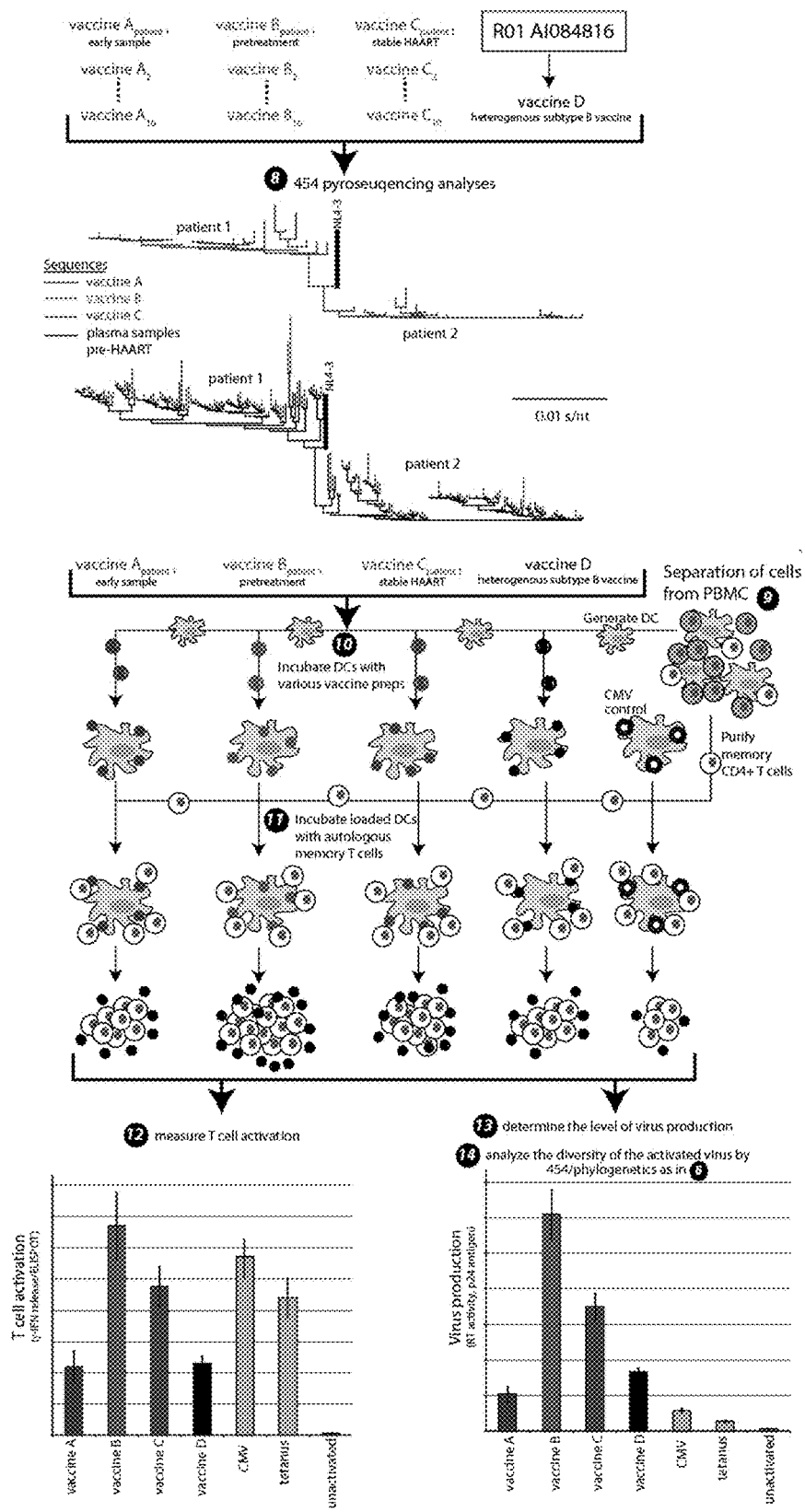

Specification includes a Sequence Listing.

Figs. 3A-C

AUTOLOGOUS HIV-1 PROTEINS FOR THE TREATMENT OF LATENT HIV-1 INFECTION

RELATED APPLICATION

This application is a Continuation of U.S. patent application Ser. No. 14/735,662, filed Jun. 10, 2015, now U.S. Pat. No. 9,642,890, which claims priority from U.S. Provisional Application No. 62/010,176, filed Jun. 10, 2014, the subject matter of which are incorporated herein by reference in their entirety.

GOVERNMENT FUNDING

This invention was made with government support under Grant No. AI49170 awarded by The National Institutes of Health, American Foundation of AIDS Research. The United States government has certain rights to the invention.

BACKGROUND

Treatment of HIV infection with antiretroviral drugs (ARVs) has markedly reduced the death rate from AIDS and improved the quality of life of HIV-infected individuals.

Combination antiretroviral drug therapy, e.g., highly active antiretroviral therapy (HAART), is very effective at suppressing HIV-1 replication, which reduces viral load from millions of HIV-1 RNA copies per ml or plasma to single copy levels, where it can be maintained indefinitely with proper treatment adherence and in the absence of adverse drug events.

HAARTs fail to eradicate the HIV-1 virus due to persistence of the virus in a long-lived pool of latently infected cells residing primarily in the resting memory $CD4^+$ T-cells population. While HAART reduces the viral load in many patients to levels below the current limits of detection, the rapid mutation rate of the HIV virus limits the efficacy of this therapy, rendering HAART ineffective in treating latent HIV infection as the virus persists in cellular reservoirs as latent proviral integrants. Continual "leaky" HIV-1 replication and activation of these latently infected cells can spur virus rebound within weeks of HAART interruption. An additional site of infection is the microglial cell and perivascular macrophage populations in the brain where activated HIV infection can lead to neurocognitive disorders even in the presence of HAART. HIV may also persist in other myeloid lineage cells and in hematopoietic stem cells.

Eliminating the latent reservoir is particularly challenging since it is established during the earliest stages of the infection. The reservoir is typically found in long-lived cells and it is likely that the reservoir can be replenished during episodes of viremia or by homeostatic replacement of latently infected cells. Complete eradication of HIV in patients is the final goal for HIV treatment, but unfeasible with current antiretroviral agents. Since intensification of antiviral regimens does not eradicate the latent pool from the infected host, there is a need to develop entirely novel forms of therapy. Most approaches to date have involved some type of cell activation through mitogens, cytokines/chemokines or HDAC inhibitors to up-regulate gene expression, which by default may also activate HIV-1 mRNA expression from latent proviruses. Unfortunately, these treatments are pleotropic and are not specifically designed for the few memory T cells harboring latent HIV-1.

SUMMARY

Embodiments herein relate to a method of reducing a latent HIV-specific memory-CD4+ T cell pool in a subject. The method includes preparing at least one HIV-1 protein coding sequence from a sample obtained from the subject, wherein the sample includes HIV-1 RNA. The method also includes introducing the at least one HIV-1 protein coding sequence into at least one expression construct using yeast homologous recombination. The method further includes transfecting a cell with the at least one expression construct, wherein the HIV-1 protein is secreted by the cell and administering a therapeutically effective amount of the secreted HIV-1 protein and a pharmaceutically acceptable carrier to the subject. The secreted HIV-1 protein stimulates latent HIV-specific memory-CD4+ T cells to induce latent HIV-1 replication resulting in HIV-specific memory-CD4+ T cell death in the subject.

Additional embodiments relate to a method of treating latent HIV infection in a subject. The method includes preparing at least one HIV-1 protein coding sequence from a sample obtained from the subject, wherein the sample includes HIV-1 RNA. The method also includes introducing the at least one HIV-1 protein coding sequence into at least one expression construct using yeast homologous recombination. The method further includes transfecting a cell with the at least one expression construct, wherein the HIV-1 protein is secreted by the cell and administering a therapeutically effective amount of the secreted HIV-1 protein and a pharmaceutically acceptable carrier to the subject. The secreted HIV-1 protein stimulates latent HIV-specific memory-CD4+ T cells to induce latent HIV-1 replication resulting in HIV-specific memory-CD4+ T cell death in the subject.

BRIEF DESCRIPTION OF THE DRAWINGS

FIGS. 1 and 2 illustrate a strategy for first examining the HIV-1 diversity in plasma and memory T cells form HIV-1 patients and representation of these populations in the autologous vaccine vectors and then determining the activation of memory T cells by autologous dendritic cells primed by different autologous vaccine candidates.

FIGS. 3(A-C) illustrate cloning of HIV-1 genes/coding sequences derived from an HIV-1 patient into pREC nfl_HIV-1/URA3 vector. (A) For creation of env chimera, the env gene is RT-PCR amplified from the patient sample and then transformed into yeast along with the linearized pREC_nfl_HIV-1Δenv/URA3 vector to obtain pREC_nfl_HIV-1/env patient. (B) Colony growth is monitored on plates following selection with specific media. (C) The HIV-lenv gene derived from three infected patients were inserted into pREC_nfl_HIV-1 Δenv/URA3 by yeast recombination and grown on C-Leu/5-FOA plates.

FIG. 4 is a schematic for the production and testing of an autologous multivalent vaccine.

FIGS. 5 and 6 illustrate the procedures used for the production of autologous multivalent vaccine vectors for patients CH1 and CH2, respectively.

FIG. 7 is a schematic of HIV-1 vaccine system in accordance with an embodiment of the present invention.

FIGS. 8 and 9 illustrate a strategy for establishing a stable SIV infection in Chinese rhesus macaques (Ch RM) and treatment with combination antiretroviral therapy (cART). The macaque model provides direct testing of the vaccine candidates in vivo and for comparison to the ex vivo human studies. Genetic diversity of the SIV population pre-and post cART in the CD4+ memory T cells in blood, lymph nodes, and gut are to be determined and the effect of autologous SIV-based therapeutic vaccines on limiting and eradicating viral reservoir is to be evaluated.

DETAILED DESCRIPTION

It should be understood that the present invention is not limited to particular methods, reagents, compounds, compositions or biological systems, which can, of course, vary. It should also to be understood that the terminology used herein is for the purpose of describing particular aspects of the present invention only, and is not intended to be limiting. Unless defined otherwise, all technical and scientific terms used herein have the same meaning as commonly understood by one of ordinary skill in the art to which the present invention pertains. Although any methods and materials similar or equivalent to those described herein can be used in the practice of the present invention, the preferred materials and methods are described herein. In describing and claiming the present invention, the following terminology will be used.

The terms "subject," "patient," "individual," and "host" used interchangeably herein, refer to a mammal, including, but not limited to, murines, felines, simians, humans, mammalian farm animals, mammalian sport animals, and mammalian pets. The term includes mammals that are infected with as well as those that are susceptible to infection by an immunodeficiency virus. In certain embodiments, the term refers to a human infected with HIV.

"HIV" is used herein to refer to the human immunodeficiency virus. It is recognized that the HIV virus is an example of a hyper-mutable retrovirus, having diverged into two major subtypes (HIV-1 and HIV-2), each of which has many subtypes. In some embodiments, a human subject is infected with the HIV-1 subtype.

As used herein, "LTR" in the context of HIV LTR means the Long Terminal Repeat, a sequence repeated at the 5' and 3' ends of the HIV genome, which consists of the enhancer and promoter regions for gene expression (U3 region), the RNA start site, and untranslated RNA sequences (RU5), such as the genomic repeat and polyadenylation sites.

As used herein, the term "viral infection" describes a diseased state in which a virus invades healthy cells, uses the cell's reproductive machinery to multiply or replicate and ultimately lyse the cell resulting in cell death, release of viral particles and the infection of other cells by the newly produced progeny viruses. Latent infection by certain viruses, e.g., HIV-1, is also a possible result of viral infection.

As used herein, "latency", "latent", "latently infected reservoir", or grammatical equivalents thereof, refer to the integration of a viral genome or an integration of a partial viral genome within a host cell genome further characterized by (i) the undetectable level of non-spliced viral RNA (<500 copies RNA/ml by a commonly used PCR assay; Chun et al., 1997, *Proc Natl Acad Sci USA*, 94:13193-13197); (ii) absence of detectable viral production; or (iii) only about $10^5$ to $10^6$ latently infected CD4 memory T cells in a subject (Williams et al., 2004, *J Biol Chem* 279(40):42008-42017). "Latency" also means a concept describing (i) an asymptomatic clinical condition; (ii) the state of viral activity within a population of cells, or (iii) the down-regulation or absence of gene expression within an infected cell. "Latency" in the context of the viral life cycle can also refer to a virus' "lysogenic phase." In contrast, a virus is in the "lytic" phase if the viral genomes are packaged into a capsid or other viral structure, ultimately leading to lysis of the host cell and release of newly packaged viruses into the host.

The term "pharmaceutical composition" refers to a preparation of one or more of the agents described herein with other chemical components, such as physiologically suitable carriers and excipients. The purpose of a pharmaceutical composition is to facilitate administration of an agent to a subject.

As used herein, "effective amount", "effective dose", "sufficient amount", "amount effective to", "therapeutically effective amount" or grammatical equivalents thereof mean a dosage sufficient to produce a desired result, to ameliorate, or in some manner, reduce a symptom or stop or reverse progression of a condition. In some embodiments, the desired result is an increase in latent HIV expression. In other embodiments, the desired result is the partial or complete eradication of a latent HIV reservoir. Amelioration of a symptom of a particular condition by administration of a pharmaceutical composition described herein refers to any lessening, whether permanent or temporary, lasting or transit that can be associated with the administration of the pharmaceutical composition.

The terms "eliminating", "eradicating" or "purging" are used interchangeably.

As used herein, "activator of latent HIV expression" means any compound that (i) can stimulate proviral latent DNA integrated into the genome of a host to begin transcription initiation, transcription elongation or replication and production of infectious virus and/or cell surface antigens, such as gp120 and/or gp41. In some embodiments, activator of latent HIV expression has an additive or synergistic effect when co-administered with pharmaceutical composition described herein. Specific examples of activators of latent HIV expression are provided herein.

As used herein, "reactivated," "reactivation" or grammatical equivalents thereof, in the context of in vivo reactivated HIV, refers to an HIV that, after a period of latency, becomes transcriptionally active, and in many instances forms infectious viral particles. The term "reactivated," as used herein in the context of in vitro reactivated HIV in a subject cell, refers to an HIV (e.g., a recombinant HIV) that, after a period of latency, becomes transcriptionally active, i.e., a functional Tat protein mediates transcription from a functional HIV promoter (e.g., a long terminal repeat promoter).

As used herein, "HAART" refers to a treatment for HIV infection which is a cocktail of anti-viral drugs known as Highly Active Anti-Retroviral Therapy. Typically, HAART includes two reverse transcriptase inhibitors and a protease inhibitor.

As recited herein, "HDAC inhibitor" or "inhibitor of HDAC" encompasses any synthetic, recombinant, or naturally-occurring inhibitor, including any pharmaceutical salts or hydrates of such inhibitors, and any free acids, free bases, or other free forms of such inhibitors capable of inhibiting the activity of a histone deacetylase (HDAC). "Hydroxamic acid derivative," as used herein, refers to the class of histone deacetylase inhibitors that are hydroxamic acid derivatives. Specific examples of inhibitors are provided herein.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof.

The term "iRNA agent," as used herein, refers to small nucleic acid molecules used for RNA interference (RNAi), such as short interfering RNA (siRNA), double-stranded RNA (dsRNA), microRNA (miRNA) and short hairpin RNA (shRNA) molecules. The iRNA agents can be unmodified or chemically-modified nucleic acid molecules. The iRNA agents can be chemically synthesized or expressed from a vector or enzymatically synthesized. The use of a chemically-modified iRNA agent can improve one or more properties of an iRNA agent through increased resistance to degradation, increased specificity to target moieties, improved cellular uptake, and the like.

The term "antisense RNA," as used herein, refers to a nucleotide sequence that comprises a sequence substantially complementary to the whole or a part of an mRNA molecule and is capable of binding to the mRNA.

The term "antibody", as used herein, is defined as an immunoglobulin that has specific binding sites to combine with an antigen.

The term "cell" and "cell line," refer to individual cells, harvested cells, and cultures containing the cells. A cell of the cell line is said to be "continuous," "immortal," or "stable" if the line remains viable over a prolonged time, typically at least about six months. To be considered a cell line, as used herein, the cells must remain viable for at least 50 passages. A "primary cell," or "normal cell," in contrast, refers to cells that do not remain viable over a prolonged time in culture. In some embodiments, the cell can be an individual cell found in a subject, particularly a subject having latent HIV infection. For example, a cell can be a resting memory CD4$^+$T cell in a subject having latent HIV infection.

The term "exogenous" refers to a moiety that is added to a cell, either directly or by expression from a gene that is not present in wild-type cells. Included within this definition of "exogenous" are moieties that were added to a parent or earlier ancestor of a cell, and are present in the cell of interest as a result of being passed on from the parent cell. "Wild-type," in contrast, refers to cells that do not contain an exogenous moiety. "Exogenous DNA" includes DNA sequences that have one or more deletions, point mutations, and/or insertions, or combinations thereof, compared to DNA sequences in the wild-type target cell, as well as to DNA sequences that are not present in the wild-type cell or viral genome.

An "isolated" plasmid, nucleic acid, vector, virus, host cell, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments described herein are increasingly more isolated. An isolated plasmid, nucleic acid, vector, virus, host cell, or other substance is in some embodiments purified, e.g., from about 80% to about 90% pure, at least about 90% pure, at least about 95% pure, at least about 98% pure, or at least about 99%, or more, pure.

The term "operably linked" refers to functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "vector" or "vector construct" is used herein to refer to a nucleic acid molecule capable transferring or transporting another passenger DNA or RNA nucleic acid molecule (i.e., a sequence or gene of interest) into a host cell. For instance, either a DNA or RNA vector can be used to derive viral particles. Similarly, a cDNA copy can be made of a viral RNA genome. Alternatively, a cDNA (or viral genomic DNA) moiety can be transcribed in vitro to produce RNA. These techniques are well-known to those skilled in the art, and also are described. A vector comprises a nucleic acid that includes the nucleic acid fragment to be transferred, and optionally comprises a viral capsid or other materials for facilitating entry of the nucleic acid into the host cell and/or replication of the vector in the host cell (e.g., reverse transcriptase or other enzymes which are packaged within the capsid, or as part of the capsid). The transferred nucleic acid (i.e., a sequence or gene of interest) is generally linked to, e.g., inserted into, the vector nucleic acid molecule. A vector may include sequences that direct autonomous replication in a cell, or may include sequences sufficient to allow integration into host cell DNA. The vector is not a wild-type strain of a virus, inasmuch as it comprises human-made mutations or modifications. Thus, the vector typically is derived from a wild-type viral strain by genetic manipulation (e.g., by addition, deletion, mutation, insertion or other techniques known in the art) to comprise lentiviral vectors, as further described herein. Useful vectors include, for example, plasmids (typically DNA plasmids, but RNA plasmids are also of use), phages, cosmids, and viral vectors.

The term "viral vector" refers to a vector that comprises a viral nucleic acid and can also include a viral capsid and/or replication functions. As will be evident to one of skill in the art, the term "viral vector" is widely used to refer to either a nucleic acid molecule (e.g., a plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s).

The term "plasmid" is meant a circular nucleic acid vector. Plasmids contain an origin of replication that allows many copies of the plasmid to be produced in a bacterial or eukaryotic cell (e.g., 293T producer cell) without integration of the plasmid into the host cell DNA.

The term "gene" refers to a nucleic acid comprising a nucleotide sequence that encodes a polypeptide or a biologically active ribonucleic acid (RNA) such as a tRNA, shRNA, miRNA, etc. The nucleic acid can include regulatory elements (e.g., expression control sequences such as promoters, enhancers, an internal ribosome entry site (IRES)) and/or introns. A "gene product" or "expression product" of a gene is an RNA transcribed from the gene (e.g., pre- or post-processing) or a polypeptide encoded by an RNA transcribed from the gene (e.g., pre- or post-modification).

Embodiments described herein relate to compositions and methods useful for reducing latent HIV-specific memory CD4+ T cells in a subject and for the treatment of latent HIV infection in a subject. It is believed that the majority of stimulated T cells in early HIV-1 infection are responding to HIV-1 antigens. These HIV-specific CD4+ T cells are highly susceptible to infection by the HIV-1 intrapatient population that is present during early disease and prior to anti-retroviral treatment (e.g., HAART). It has been shown that the HIV-specific resting memory CD4+ T cells are most responsive to the autologous virus that was present in a subject during early disease and prior to HAART. Thus, the present invention provides methods of activating those memory T cells specific to early infection HIV-1 antigens as these HIV-1 specific T cells harbor the majority of a subjects' latent HIV-1 pool.

In some embodiments, yeast-based cloning methods can be used to produce therapeutic multivalent HIV-1 vaccine vectors including one or more protein coding sequences derived from the autologous HIV-1 population found in a subject during early disease and prior to HAART. It is contemplated that when administered to an HIV infected subject, therapeutic multivalent HIV-1 vaccine vectors described herein can activate resting memory CD4+ T cells that are responsive to the autologous virus thereby eliminating the majority of the latent HIV-1 population in the subject.

Aspects described herein therefore provide a method of reducing latent HIV-specific memory $CD4^+$ T cell pool in a subject. The HIV-specific memory CD4+ T-cells activated by therapeutic multivalent HIV-1 vaccine vectors described herein can stimulate replication of latent virus and ultimately lead to HIV-specific memory T-cell death by apoptosis, necrosis or elimination by another T cell (i.e. HIV-specific cytotoxic T-lymphocytes), and the virus produced from these cells can then be inhibited or treated via one or more antiretroviral drugs.

In some embodiments, the method can include the step of preparing at least one HIV-1 protein coding sequence from a biological sample obtained from the subject, wherein the sample includes HIV-1 RNA.

The HIV-1 protein coding sequence prepared in accordance with the present invention can include HIV-1 envelope (env), gag and/or pol protein coding sequences and combinations thereof. In some embodiments the HIV-1 protein coding sequence is an HIV-1 gag/pol protein or an env coding sequence.

Any HIV-1 gag (group-specific antigen) protein coding sequence, or fragment thereof, derived from an HIV-1 virus of a subject can be used. Exemplary gag protein coding sequences derived from an HIV-1 virus include gag protein coding sequences for the precursor gag polyprotein, which is processed by viral protease during maturation to MA (matrix protein, p17); CA (capsid protein, p24); SP1 (spacer peptide 1, p2); NC (nucleocapsid protein, p7); SP2 (spacer peptide 2, p1) and P6 protein.

Any HIV-1 pol protein coding sequence, or fragment thereof, derived from an HIV-1 virus of a subject can be used. Exemplary pol protein coding sequences derived from an HIV-1 virus include pol protein coding sequences for viral enzymes reverse transcriptase (RT) and RNase H, integrase (IN), and HIV protease (PR).

Any HIV-1 envelope protein coding sequence, or fragment thereof, derived from an HIV-1 virus of a patient that mediates membrane fusion can be used. As used herein, the term "HIV-1 envelope protein" refers to a full-length protein, near full length protein, fragment, analog, or derivative thereof. The HIV-1 envelope protein coding sequence derived from an HIV-1 virus of an HIV-1 infected subject may be a sequence coding a surface glycoprotein.

HIV-1 envelope protein coding sequences useful in the present method can include, but are not limited to HIV-1 envelope protein coding sequences encoding surface proteins from a number of different HIV-1 groups. Exemplary HIV-1 groups include both the "major" group (i.e., the M group) and the minor groups O, N and P. An HIV-1 envelope protein useful in the present method can also include subgroups, or clades, of HIV-1 groups known in the art.

In some embodiments, the HIV-1 envelope protein coding sequence can encode a surface protein from a patient infected with a HIV-1 group M subtype B variant. Non-limiting examples of group M subtype B HIV-1 variants can include HIV-1B-92BR014, HIV-1B-92TH593, HIV-1B-92US727, and HIV-1B-92US076.

In some embodiments, the HIV-1 envelope protein coding sequence encodes a surface protein from a subject infected with an HIV-1 group M non-subtype B variant. Non-B HIV-1 group M variants can include the clades or subtypes A, C, D, F, G, H, J, K, N and circulating recombinant forms derived from recombination between viruses of different subtypes. Non-limiting examples of non-B HIV-1 subtypes include three subtype A (HIV-1A-93RW024, HIV-1A-92UG031, and HIV-1A-92UG029), four subtype C (HIV-1C-96USNG58, HIV-1C-93MW959, HIV-1C-98IN022, and HIV-1C-92BR025), five subtype D (HIV-1D-92UG021, HIV-1D-92UG024, HIV-1D-94UG114, HIV-1D-92UG038, and HIV-1D-93UG065), two subtype F (HIV-1F-93BR20 and HIV-1F-93BR29), two subtype G (HIV-1G-RU132 and HIV-1G-RU570), and six circulating recombinant forms (HIV-1AE-CMU02, HIV-1AE-CMU06, HIV-1AE-92TH021, HIV-1AE-93TH051, HIV-1AE-95TH001, and HIV-1BF-93BR029).

Typically, the biological sample is obtained from a subject following infection with and/or diagnosis of an HIV infection in the subject. It has been found that HIV-specific resting memory CD4+ T cells are most responsive to the autologous virus that was present in a subject during early disease and prior to initiating anti-retroviral treatment (e.g., highly active antiretroviral therapy (HAART)). Therefore, in some embodiments, the biological sample is obtained from a subject following HIV-1 infection but prior to the subject initiating anti-retroviral treatment. In certain embodiments, the biological sample is obtained from a subject following HIV-1 infection but prior to the subject initiating HAART.

Samples obtained from a subject can include blood samples. In certain embodiments, the sample is a blood plasma sample. In some embodiments, a blood sample can be collected from a patient and plasma samples can be processed for immediate use. Alternatively, a processed plasma sample can be stored at −80° C. for analysis at a later time.

In some embodiments, a blood sample obtained from the HIV-infected patient has a viral load ranging from about <50 to about 10,000 copies of viral RNA/ml. In some embodiments, the viral load can range from about 1000 to about 10,000 copies of viral RNA/ml. In certain embodiments, a blood sample from the HIV-infected patient has a viral load ≥1,000 copies of viral RNA/ml.

In some embodiments, plasma viral HIV-1 RNA coding for at least one HIV-1 coding sequence can be purified from pelleted virus particles using well known methods. In an exemplary embodiment, plasma viral HIV-1 RNA can be purified from pelleted virus particles by centrifuging one milliliter of a patient's plasma at 20,000 g×60 min at 4° C. using a QIAamp Viral RNA Mini Kit (Qiagen).

Once the plasma HIV-1 RNA is obtained and purified it can be reverse transcribed into HIV-1 cDNA using well known methods. An example of a protocol for the preparation of HIV-1 cDNA from purified HIV-1 RNA includes adding 10 µl of the backward (BWD) primer EXT TAT REC CON BWD 13 having SEQ ID NO: 10 to 7.25 µl of DEPC-treated $H_2O$, 2.0 µl of RT Buffer 10× and 2.0 µl of 10 mM dNTP mix. This mixture is further added to 5 µl of purified HIV-1 RNA and 40 of PCR water and incubated at 88° C. for 1 minute, 65° C. for 10 minutes, and then 25° C. for 5 min. The resulting mixture can then be kept at room temperature. Next, 2.0 µl of 100 mM DTT, 0.25 µl (10U)

RNase inhibitor, and 0.5 μl AccuScript High-Fidelity Reverse Transcriptase (AccuRT) (STRATAGENE) is added individually to the mixture. The mixture is then incubated at 42° C. for 90 min, heat inactivated at 70° for 15 minutes, and chilled and held at 4° for PCR amplification. Alternatively, the mixture can be frozen at −20° for later amplification.

Additional backward primers for the preparation of HIV-1 cDNA from purified HIV-1 RNA are disclosed in Table 1 below.

TABLE 1

Oligonucleotide backward (BWD) primers for the preparation of HIV-1 cDNA from purified HIV-1 RNA derived from a patient.

| Primer Name | Location | Sequence |
| --- | --- | --- |
| EXT TAT REC CON BWD 11 | 8699→8748 | SEQ. ID. NO. 8 |
| EXT TAT REC CON BWD 12 | 8640→8689 | SEQ. ID. NO. 9 |
| EXT TAT REC CON BWD 13 | 8562→8611 | SEQ. ID. NO. 10 |

A portion of the HIV-1 cDNA corresponding to an HIV-1 env, gag and/or pol protein coding sequence derived from the patient can be amplified using a PCR assay where the patient derived HIV-1 cDNA acts as a template. In an exemplary embodiment, PCR amplification of the envelope protein coding sequence can amplify a portion of the patient's env gene from gp120 up to Tat exon 2. In another embodiment, PCR amplification of the envelope protein coding sequence can amplify a 2302 nt fragment of the HIV-1 env gene, including the entire surface glycoprotein (gp120) and a portion of the transmembrane glycoprotein (gp41).

The use of both external and nested env, gag and/or pol gene specific primers (i.e., a nested PCR) can be employed to amplify an HIV-1 envelope protein coding sequence of patient derived HIV-1 cDNA. In an exemplary embodiment, the external forward primer TAT REC CON FWD 3 having SEQ ID NO: 3 and the external backward primer TAT REC CON BWD 7 having SEQ ID NO: 7 can be employed in combination with the nested forward primer IntF gp120.3 having SEQ ID NO: 11 and the nested backward primer TAT REC CON BWD 4 having SEQ ID NO: 4 for the amplification of a 2,302 nt fragment including all the surface glycoprotein (gp120) and most of the transmembrane glycoprotein (gp41) coding sequence of the patient's env gene, missing only 321 nt of the gp41 cytoplasmic domain that retains the N-terminal portion.

Additional external and nested env gene specific primers for amplifying a portion of the HIV-1 cDNA corresponding to an HIV-1 envelope protein coding sequence derived from a patient are disclosed in Table 2 below.

TABLE 2

Oligonucleotide forward (FWD) and backward (BWD) external primers and nested primers for the insertion of HIV-1 envelope protein coding sequence derived from a patient into pREC nfl HIV-1 envΔ/URA3 vectors to create patient derived pREC nfl HIV-1 vectors

| TAT REC CON FWD 1 | 5758→5808 | SEQ. ID. NO. 1 |
| --- | --- | --- |
| TAT REC CON FWD 2 | 5732→5782 | SEQ. ID. NO. 2 |

TABLE 2-continued

Oligonucleotide forward (FWD) and backward (BWD) external primers and nested primers for the insertion of HIV-1 envelope protein coding sequence derived from a patient into pREC nfl HIV-1 envΔ/URA3 vectors to create patient derived pREC nfl HIV-1 vectors

| TAT REC CON FWD 3 | 5713→5762 | SEQ. ID. NO. 3 |
| --- | --- | --- |
| TAT REC CON BWD 4 | 8425→8474 | SEQ. ID. NO. 4 |
| TAT REC CON BWD 5 | 8429→8478 | SEQ. ID. NO. 5 |
| TAT REC CON BWD 6 | 8439→8488 | SEQ. ID. NO. 6 |
| Int Fwd gp120.3 | 6179→6198 | SEQ. ID. NO. 11 |
| Int Fwd gp120.4 | 6146→6165 | SEQ. ID. NO. 12 |

Amplified PCR products corresponding to a patient derived HIV-1 envelope, gag and/or pol protein coding sequence (i.e., the patient derived amplicon) can then be purified for use in the next step of the method. For example, PCR cDNA products corresponding to the gp120/gp41-coding regions of an HIV-1 envelope protein derived from a patient can be purified using a QIAquick PCR Purification Kit (QIAGEN).

The method further includes the step of introducing the at least one patient derived HIV-1 protein coding sequence into at least one expression construct. In some embodiments, a patient derived HIV-1 protein coding sequence can be introduced into an expression construct using a yeast based homologous recombination/gap repair method. An exemplary yeast-based HIV-1 cloning methodology for use in a method described herein that adopts yeast recombination/gap repair to introduce nearly any HIV-1 coding region (as a PCR product) into a DNA vector is disclosed in Dudley, D. M.; Gao, Y.; Nelson, K. N.; Henry, K. R.; Nankya, I.; Gibson, R. M.; Arts, E. J. A novel yeast-based recombination method to clone and propagate diverse HIV-1 isolates. *Biotechniques* 2009, 46, 458-467, which is herein incorporated by reference in its entirety.

An expression construct can include a vector, such as a plasmid. A suitable vector includes at least one origin of replication, a region of the DNA that is substantially identical to the primer binding site (pbs) of HIV-1, a selectable gene replacing at least a portion of the env, gag, and/or pol gene of HIV-1, and a region of DNA that is substantially identical to the 3' end of the long terminal repeat region of HIV. By "substantially identical", it is meant that the regions have sufficient homology with the named segments of DNA as to be able to hybridize under stringent conditions.

A suitable vector can also comprise a partial retrovirus genome, specifically; a vector can include a near full length (nfl) HIV-1 genome devoid of the 5' LTR. Lack of a 5' LTR allows the HIV-1 genome to be located precisely in front of the CMV promoter in the vector such that transcription would be initiated at the first nucleotide of the primer binding site. Cloning the HIV-1 sequence in this way could not be performed with restriction enzymes but can be performed by yeast recombination. In addition, a vector devoid of the HIV-1 5' LTR is unable to produce infectious virus. Vectors can include the essential elements for plasmid growth in bacteria and for HIV-1 expression in human cells.

Suitable vectors for use in the invention can include a sequence corresponding to a near full length HIV-1 backbone. In some embodiments, the near full length HIV-1 backbone includes an HIV-1 Group M subtype B backbone (e.g., HIV-1$_{NL4-3}$). In certain embodiments, the vector can recombine with not only homologous env, gag and/or pol protein coding sequences derived from patients infected with Group M subtype B wild-type and multidrug resistant strains of HIV-1 but also from sequences derived from patients infected with other non-B HIV-1 group M subtypes. Therefore, in some embodiments the near full length HIV-1 backbone of a vector can include a minor HIV-1 group backbone. Exemplary minor HIV-1 group backbones can include Group N, Group O and Group P strains near full length HIV-1 backbones.

In certain embodiments, the near full length HIV-1 yeast-based vector pREC nfl HIV-1 Δenv/URA3 is employed. pREC nfl HIV-1 Δenv/URA3 contains the selection marker URA3. URA3 encodes the orotidine-5′-phosphate decarboxylase protein involved in the bio-synthesis of uracil. To prepare pREC nfl HIV-1 Δenv/URA3, URA3 is recombined in yeast to replace a section of the env gene in the pREC nfl HIV-1 vector resulting in a vector having the pREC nfl HIV-1 sequence except with a URA3 gene inserted into and replacing a portion of the envelope gene. Successful recombinants may be selected by growing the yeast transformed with the URA3 and the pREC nfl HIV-1 on uracil-deficient media. In certain embodiments, at least a portion of the 5′ and 3′ ends of the pREC nfl HIV-1 env gene remain so as to permit further recombination.

Some of the most commonly applied selection marker genes are wild-type alleles of yeast genes that encode key enzymes in the metabolic pathways towards essential monomers used in biosynthesis. An example is the URA3 gene, which encodes orotidine-5′-phosphate decarboxylase, an essential enzyme in pyrimidine biosynthesis in *Saccharomyces cerevisiae*. In addition to URA3, a pREC nfl HIV-1 Δenv/URA3 vector can also include a yeast transformation selection marker gene that does not replace a portion of the envelope gene (e.g., the HIS3, LEU2, TRP1, and MET15 marker genes which encode essential enzymes for de novo synthesis of the amino acids L-histidine, L-leucine, L-tryptophan, and L-methionine, respectively). Use of these genes as markers is restricted to host strains that are auxotrophic for the nutrient in question due to the absence of a functional chromosomal copy of the marker gene. Unless transformed to prototrophy with a functional allele of the marker gene, auxotrophic yeast strains can be propagated only in media that contain the appropriate growth factor(s). This nutritional complementation may be achieved either by including the growth factors in defined synthetic media or by using complex medium components (e.g., yeast extract and peptone) that are rich in the relevant growth factors.

Expression constructs can be made, for example, by replacing various portions of the HIV-1 env, gag and/or pol gene in yeast-based vectors, such as the pREC nfl HIV-1 vector, with a selectable marker such as URA3. In some embodiments, URA3 may be inserted into the pREC nfl HIV-1 vector at different sites for replacement of the gp120/gp41, the gp120, or V3 coding sequence in the HIV-1 envelope gene, for example. A list of near full length HIV-1 isolates containing a URA3 substitution for use in the present invention is provided in Table 3.

TABLE 3 pREC nfl HIV-1 vectors with various coding region replacements with URA3

| pREC-$_{NFL-HIV-1}$ Deletions | Location of Deletion in NL4-3 | Size of Deletion |
|---|---|---|
| Δenv\URA3 | 6221-8785 | 2565 |
| Δenv-s\URA3 | 6221-8264 | 2043 |
| Δenv gp120\URA3 | 6221-7747 | 1527 |
| Δenv gp120 v1/v2\URA3 | 6611-6802 | 192 |
| Δenv gp120 v3\URA3 | 7100-7207 | 108 |
| Δenv gp120 v4/v5\URA3 | 7368-7627 | 260 |
| Δenv gp41\URA3 | 7748-8785 | 1038 |
| Δenv gp41-s\URA3 | 7748-8264 | 517 |

To insert a purified HIV-1 protein coding sequence derived from a subject and replace a selectable gene encoded by the vector, a yeast strain (e.g., Strain BY4727) may be transformed with either linearized or non-linearized pREC_nfl_HIV-1Δproteome/URA3, using a lithium acetate technique for example, along with the purified HIV-1 protein coding cDNA sequence derived from a patient. The patient derived cDNA recombines with the remaining portions of the env, gag and/or pol gene flanking the URA3 gene in pREC nfl HIV-1 Δproteome/URA3. The resulting recombinants contain a near full length HIV-1 sequence from the NL4-3 HIV-1 strain, with a patient-derived env, gag and/or pol gene or gene fragment replacing the env, gag and/or pol gene of NL4-3.

In an exemplary embodiment, PCR products spanning the gp120/gp41-coding region of HIV-1 derived from a patient are introduced via yeast homologous recombination into a pRECnfl ΔEnv/URA3 vector. For example, the pRECnfl-TRPΔEnv/URA3 vector includes a near-full length HIV-1 genome where a yeast uracil biosynthesis (URA3) gene and a TRP yeast transformation marker have replaced the native gp120/gp41 HIV-1 coding sequence. Following successful yeast homologous recombination of the gp120/gp41-coding region of HIV-1 derived from a patient and the pRECnfl-TRPΔEnv/URA3 vector, the vector construction expresses all HIV-1 coding regions, that is, all genes corresponding to the HIV-$1_{NFL4-3}$ strain used as backbone in the vector plus the patient-derived HIV-1 envelope protein coding sequence; however, it is unable to produce infectious virus since it is missing the 5' LTR region. In another embodiment, PCR products spanning the gp120/gp41-envelope coding region of HIV-1 derived from a patient are introduced via yeast homologous recombination into a pREC_SIN_HIV-1ΔEnv/URA3 vector.

In another exemplary embodiment, PCR products spanning both the gag and pol (i.e., gag/pol) coding region of HIV-1 derived from a patient are introduced via yeast homologous recombination into a pRECnfl Δgag-pol/URA3 vector (e.g., pREC_exp_HIV-1 Δgag-pollURA3). The pRECnfl-Δgag-pol/RA3 vector includes a near-full length HIV-1 genome where a yeast uracil biosynthesis (URA3) gene has replaced at least a portion of the native gag/pol HIV-1 coding sequence.

Yeast colonies containing a recombined sequence in the pREC nfl HIV-1 vectors, for example, where a URA3 gene has been replaced by the HIV-1 env, gag and/or pol protein coding sequence derived from a patient, may be selected on plates containing a selection agent, such as CMM-Leu+5-Fluoro-1,2,3,6-Tetrahydro-2,6-Dioxo-4-Pyrimidine Carboxylic Acid (FOA). FOA is converted to the toxic substrate 5-fluorouracil by the URA3 gene product, orotidine-5'-phosphate decarboxylase. FOA-resistant yeast including the newly recombined expression construct can then be grown in yeast complete minimal medium. In one example over 95%-98% of all yeast colonies following transfection harbor vectors with the correct subject derived insert and in the correct reading frame due to highly specific recombination.

Organisms other than yeast may also be utilized to provide homologous recombination. For example, the bacterial strains TB10-pyrF287 and TB10ΔpyrF can also be used for recombination of patient derived HIV-1 envelope, gag and/or pol protein coding sequences into the pREC nfl HIV-1 plasmids. TB10ΔpyrF strain genotype is nad::Tn10/pλ-≠cro-bro tetr pyrF. TB10ΔpyrF287 strain genotype is nad::Tn10/pλ-Δcro-bro tetr pyrF287. These strains express λ bet, gam, and exo for hyper-recombination. Additionally, pyrF is the homolog to URA3. Deleting and mutating pyrF in TB10-pyrF287 and TB10λpyrF can allow URA3 plasmids to be used for selection. This will allow the same plasmids to be currently used in the yeast system to be used in the bacterial system.

Moreover, as shown in the Example section below, the yeast-based cloning system allows for the cloning of a simian immunodeficiency virus (SIV) protein coding sequence obtained from an infected animal into an acceptable expression construct. Exemplary expression constructs can include SIVmac, SIVcpz, and SHIV molecular phage or plasmid clones wherein such constructs can be utilized in a method of reducing latent SIV-specific memory-CD4+ T cells in simians.

Following successful homologous recombination, the at least one expression construct can then be extracted and purified from the organism providing recombination. For example, recombined pREC nfl HIV-1 vectors including the HIV-1 envelope, gag and/or pol protein coding sequence(s) derived from a patient can be purified from the entire number of yeast colonies. In some embodiments, an expression construct is extracted and purified from about 200 to greater than 1000 individual yeast colonies.

The purified expression construct can then be transformed into bacteria (e.g., *E. coli*) for plasmid vector propagation. In an exemplary embodiment, Electrocomp TOP10 *E. coli* bacteria cells (Invitrogen) are transformed with purified recombined pREC nfl HIV-1 vectors. Plasmid DNA, once purified from the bacteria, can be stored at −80° C. until further use. In an alternative embodiment, bacterial colonies can be transformed with crude yeast extract without the purification step. In some embodiments, transformed bacterial colonies can be screened for the env, gag and/or pol insert and absence of the URA3 gene using well known methods.

The method then further includes the step of transfecting a cell with the at least one expression construct. In some embodiments, a cell is transfected with one, two or three expression constructs each including at least one HIV-1 coding sequences derived from a subject and/or an HIV-1 backbone sequence. Methods of transfecting and expressing genes in mammalian cells are known in the art. Transducing cells with viral vectors can involve, for example, incubating vectors with cells within the viral host range under conditions and concentrations necessary to cause transduction. See, e.g., Methods in Enzymology, vol. 185, Academic Press, Inc., San Diego, Calif. (D. V. Goeddel, ed.) (1990) or M. Krieger, Gene Transfer and Expression—A Laboratory Manual, Stockton Press, New York, N.Y.; and Muzyczka (1992) Curr. Top. Microbiol. Immunol. 158: 97-129, and references cited in each. The culture of cells, including cell lines and cultured cells from tissue samples is well known in the art. Freshney (Culture of Animal Cells, a Manual of Basic Technique, Third edition Wiley-Liss, New York (1994)) provides a general guide to the culture of cells.

An expression construct for use in transfecting a cell in a method of the invention can include a vector, such as a plasmid. Suitable vectors for use in eukaryotic and prokaryotic cells are known in the art and are commercially available or readily prepared by a skilled artisan. Additional vectors can also be found, for example, in CURRENT PROTOCOLS IN MOLECULAR BIOLOGY (Ausubel, F. M., et al., eds. 2000) and Sambrook et al., "Molecular Cloning: A Laboratory Manual," 2nd ED. (1989), the teachings of which are incorporated herein by reference. In some embodiments, transformation of a cell with a reporter molecule fragment sequence can be achieved using calcium phosphate, DEAE-dextran, electroporation, cationic lipid reagents, or any other convenient technique known in the art.

In some embodiments, an expression vector for transfecting a cell is a mammalian expression vector including a promoter operably linked to a reporter molecule fragment expression sequence. For example, a CMV promoter-based vector can be used. Human cytomegalovirus (CMV) promoter regulatory region drives constitutive protein expression. In certain embodiments, the expression vector is a pCMV_cplt expression vector. The pCMV_cplt expression vector can be constructed by PCR-amplifying the cytomegalovirus (CMV) sequence from pcDNA3.1zeo/CAT (Invitrogen). The TOPO vector was then subjected to digestion by MLUI and BstXI to generate a CMV promoter-driven R, U5 and gag fragment. The resulting fragment is cloned back into the pcDNA3.Izeo/CAT backbone to generate the pCMV_cplt vector.

Any cell can be transfected in accordance with the present method. The cell can be human or nonhuman. The cell can be freshly isolated (i.e., primary) or derived from a short term- or long term-established cell line. In one embodiment, the first is a eukaryotic cell, where the eukaryotic cell is a cell that can be grown in culture, using standard laboratory procedures and media well known to those of skill in the art. The cell may be any cell that is not susceptible to toxic effects of chronically expressing viral proteins and that permit cell surface expression of such proteins. In some embodiments, the cell is a cell that does not express complete complementary cell surface receptors or co-receptors for the expressed patient-derived HIV-1 env coded protein and therefore will not undergo fusion with itself.

Exemplary biological cell lines include NIH-3T3 murine fibroblasts, quail QT6 cells, canine Cf2Th thymocytes, Mv1 Lu mink lung cells, Sf9 insect cells, primary T-cells, human T-cell lines (e.g., H-9), U-87 MG glioma, SCL1 squamous cell carcinoma cells, CEM, HeLa epithelial carcinoma, Chinese hamster ovary (CHO) cell, SF33 cell and HEK293T cell. Such cell lines are described, for example, in the Cell Line Catalog of the American Type Culture Collection (ATCC, Rockville, Md.). In one embodiment, the first cell is a HeLa epithelial carcinoma cell or a human HEK293T cell.

In one embodiment, a cell stably expresses the patient-derived HIV-1 protein and secretes it from the cell surface. The cell can include at least one expression construct made up of a suitable promoter operably linked to the patient-derived HIV-1 viral protein encoding sequence, where the expression construct is integrated into the cell genome in a manner such that the coding sequence is expressed in the cell and the expressed viral protein is transported to the cell surface where it is secreted. For example, a cell may comprise a coding sequence for the patient-derived HIV-1 protein stably integrated into its genome in a manner such that it is expressed in the cell and directed to the cell surface where it is secreted into the surrounding media. Once secreted into the media, the HIV-1 protein can be harvested for therapeutic use as described below. In some embodiments, the HIV-1 protein is harvested about 48 to about 72 hours post-transfection. Harvested HIV-1 protein can then be purified for example, through the use of sucrose-cushion centrifugation, and then quantified for capsid/p24 content.

In a specific embodiment, the patient-derived HIV-1 protein secreted by the cell is a defective HIV-1 particle including env, gag and pol coded proteins in the correct stoichiometry and is morphologically indistinguishable from a wild type HIV-1. For example, the cloning system described herein allows for the pREC HIV-1 nfl plasmid upon 293T transfections to produce vectors that lack 5'LTR and as such cannot initiate reverse transcription, lack a functional reverse transcriptase enzyme, lack genomic RNA due to deletion of Ψ packaging element, contain a full complement of HIV-1 proteins in the correct stoichmetry, and are dead but morphologically identical to wild type.

In another exemplary embodiment, a 293T cell is transfected with a pREC_exp_HIV-1 Δgag-pol/URA3 and a pREC_SIN_HIV-1ΔEnv/URA3 derived from a subject having HIV-1, and a pCMV_cplt expression vector expressing defective genomic RNA. As shown in FIG. 1a, the transfected cell constantly expresses the resulting vaccine construct. The separate Gag-Pol vector will support virus production but the mRNA cannot be preferentially encapsidated or if randomly encapsidated at low frequencies, will not support reverse transcription/proviral DNA synthesis.

Once a nucleic acid is incorporated into a cell as provided herein, the cell can be maintained under suitable conditions for constant expression of the exogenous patient-derived HIV-1 viral protein. Generally, the cells are maintained in a suitable buffer and/or growth medium or nutrient source for growth of the cells and expression of the gene product(s). Exemplary growth medium can include, but is not limited to, DMEM medium/L-glutamine (GIBCO;CELLGRO;MEDIATECH) supplemented with FBS (CELLGRO), penicillin/streptomycin (GIBCO), puromycin and G418 (MEDIATECH).

The method also includes the step of administering a therapeutically effective amount of the secreted HIV-1 protein and a pharmaceutically acceptable carrier to the subject. As discussed above, it is contemplated that the patient-derived HIV-1 protein stimulates latent HIV-specific memory CD4+ T cells to induce latent HIV-1 replication which results in HIV-specific memory T cell death in the patient subject thereby reducing the latent HIV-specific memory-CD4+ T cell pool in the subject.

Optimal dosages to be administered may be readily determined by those skilled in the art, and will vary with the particular compound used, the strength of the preparation, the mode of administration, and the advancement of the disease condition. In addition, factors associated with the particular patient being treated, including patient age, weight, diet and time of administration, will result in the need to adjust dosages.

In some embodiments, a pharmaceutical composition including an HIV-1 protein or particle derived from the subject described herein can be administered in combination with one or more additional activators of latent HIV expression. In certain embodiments, such a combination can synergistically enhance reactivation of latently infected cell populations of cells compared to either agent alone.

In these embodiments, the HIV-1 protein derived from the subject can be provided in a composition that can also include an activator of latent HIV expression. Several activators of latent HIV expression can be used in the compositions and methods described herein. For example, an additional activator of latent HIV expression can include, but is not limited to, histone deacetylase (HDAC) inhibitors and protein kinase C agonists.

It has been demonstrated that HDAC inhibitors induce the transcriptional activation of the HIV-1 promoter. An HDAC inhibitor of the present invention may be any molecule that effects a reduction in the activity of a histone deacetylase. This includes proteins, peptides, DNA molecules (including antisense), RNA molecules (including iRNA agents and antisense) and small molecules. In some embodiments of the present invention, a HDAC inhibitor is a small interfering RNA (siRNA), for example, a si/shRNA directed against HDAC1, 2, 3, 4, 5, 6, 7, 8, 9, 10, or 11. Non-limiting examples of such HDAC inhibitors are set forth below. It is understood that HDAC inhibitors include any salts, crystal structures, amorphous structures, hydrates, derivatives, metabolites, stereoisomers, structural isomers, and prodrugs of the HDAC inhibitors described herein.

In some embodiments, an HDAC inhibitor can include short-chain fatty acids (e.g., Sodium Butyrate, Isovalerate, Valerate, 4-Phenylbutyrate (4-PBA), Phenylbutyrate (PB), Propionate, Butyramide, Isobutyramide, Phenylacetate, 3-Bromopropionate, Tributyrin, Valproic acid (Vpa), Valproate, Valproate semisodium and pivaloyloxymethyl butyrate (PIVANEX)).

In other embodiments, an HDAC inhibitor can include a hydroxamic acid derivative (e.g., suberoylanilide hydroxamic acid (SAHA, vorinostat), Trichostatin analogs such as Trichostatin A (TSA) and Trichostatin C, m-Carboxycinnamic acid bishydroxamide (CBHA), Pyroxamide, Salicylbishydroxamic acid, Suberoyl bishydroxamic acid (SBHA), Azelaic bishydroxamic acid (ABHA) Azelaic-1-hydroxamate-9-anilide (AAHA), 6-(3-Chlorophenylureido) carpoic hydroxamic acid (3Cl-UCHA), Oxamflatin [(2E)-5-[3-[(phenylsulfonyl) amino]phenyl]-pent-2-en-4-ynohydroxamic acid], A-161906 Scriptaid, PXD-101 (Prolifix), LAQ-824, CHAP,MW2796, MW2996; or any of the hydroxamic acids disclosed in U.S. Pat. Nos. 5,369,108, 5,932,616, 5,700,811, 6,087,367, and 6,511,990). In certain embodiments, the HDAC inhibitor is SAHA.

In still other embodiments, an HDAC inhibitor can include benzamide derivatives (e.g., CI-994; MS-275 [N-(2-aminophenyl)-4-[N-(pyridin-3-yl methoxycarbonyl) aminomethyl]benzamide] and 3'-amino derivative of MS-275).

In yet other embodiments, an HDAC inhibitor can include cyclic peptides (e.g., Trapoxin A (TPX)-cyclic tetrapeptide (cyclo-(L-phenylalanyl-L-phenylalanyl-D-pipecolinyl-L-2-amino-8-oxo-9,10-epoxy decanoyl)), FR901228 (FK 228, depsipeptide), FR225497 cyclic tetrapeptide, Apicidin cyclic tetrapeptide [cyclo(N—O-methyl-L-tryptophanyl-L-isoleucinyl-D-pipecolinyl-L-2-amino-8-oxodecanoyl)], Apicidin Ia, Apicidin Ib, Apicidin Ic, Apicidin IIa, and Apicidin IIb, CHAP, HC-toxin cyclic tetrapeptide , WF27082 cyclic tetrapeptide, and Chlamydocin.

Additional HDAC inhibitors can include natural products, such as psammaplins and Depudecin, Electrophilic ketone derivatives such as Trifluoromethyl ketones, α-keto amides such as N-methyl-α-ketoamides, LSD1 polypeptide, TNF-alpha (TNFα), an inducible transcription factor NF-AT (nuclear factor of activated T cells), and Anti-IκBα or IκBε agents.

Protein kinase C (PKC) agonists can include non-tumor-promoting phorbol deoxyphorbol esters such as prostratin, the structural or functional analogs thereof described in US20120101283 A1, 12-deoxyphorbol 13-phenylacetate (DPP), Ingenol mebutate (ingenol-3-angelate, tradename PICATO) and bryostatins such as bryostatin-1.

In some embodiments, a composition including an HIV-1 protein derived from the subject can be administered to or contacted with a cell of the subject having a latent HIV infection. The administration can be in vivo, for example, by an intradermal, intravenous, subcutaneous, oral, aerosol, intramuscular and intraperitoneal route, or ex vivo, for example, by transfection, electroporation, microinjection, lipofection, adsorption, protoplast fusion, use of protein carrying agents, use of ion carrying agents, and use of detergents for cell permeabilization.

In some embodiments, the HIV-1 protein derived from the subject and the activator of latent HIV expression are contacted simultaneously with the HIV infected cell. This can be done by contacting the cell with a composition comprising both compounds as described herein. In other embodiments, the activator of latent HIV expression and the HIV-1 protein derived from the subject are contacted with the HIV infected cell sequentially.

The methods described herein can be applied to any cell of the subject wherein an HIV genome is integrated into the cellular DNA. The cell can include a resting lymphoid mononuclear cell obtained from a mammal including e.g., lymphocytes, such as T cells (CD4, CD8, cytolytic, helper), B cells, natural killer cells; mononuclear phagocytes, such as monocytes, macrophages, epitheloid cells, giant cells, Kupffer cells, alveolar macrophages; dendritic cells, such as interdigitating dendrite cells, Langerhans cells, or follicular dendritic cells; granulocytes; etc. In certain embodiments, the cell is a $CD4^+$ T cell, such as a resting memory $CD4^+$ T-cell.

HIV-1 proteins derived from a subject alone or in combination with the activators of latent HIV expression described herein, are also useful in the manufacture of pharmaceutical compositions. The pharmaceutical composition can include a therapeutically effective amount of the HIV-1 protein derived from the subject alone or in combination with the activators of latent HIV expression along with excipients or carriers suitable for either enteral or parenteral administration to a subject. It is contemplated that a therapeutically effective amount of a pharmaceutical composition described herein can be administered to a subject for the treatment of, for example, latent HIV infection.

Therefore, in another aspect, a pharmaceutical composition described herein can be employed in a method for treating HIV latency in a subject. The subject can include a host latently infected with HIV, e.g., a human latently infected with HIV. The subject can include a subject having a persistant HIV reservoir despite treatment with antiretroviral therapy (e.g., HAART). Thus, in some embodiments, the therapeutically effective amount is the amount of a pharmaceutical composition to significantly decrease a latent HIV reservoir in a latently HIV infected subject.

A therapeutically effective amount of a pharmaceutical composition including an HIV-1 protein derived from a subject can be administered to the latently HIV-infected subject. A pharmaceutical composition may include any combinations of HIV-1 protein derived from a subject, and optionally activators of latent HIV expression compounds described herein along with a pharmaceutically acceptable carrier.

It is expected that a combination therapy including an HIV-1 protein derived from the subject and one or more activators of latent HIV expression is therapeutically effective for the treatment of latent HIV infection as such a therapy can purge the latent HIV from a subject's body since harboring cells with reactivated HIV can be recognized by specific CTLs (cytotoxic CD8+ T cells), by NK (Natural Killer) cells and by specific cytotoxic antibodies. It is also expected that a combination therapy including the use of one or more activators of latent HIV in a subject described herein can purge the latent HIV from a subject's body by targeting and neutralizing the reactivated HIV-1 using anti-retroviral therapy, e.g., HAART.

Therefore, in some embodiments, a pharmaceutical composition administered to a subject includes a therapeutically effective amount of an HIV-1 protein derived from the subject, an activator of latent HIV expression, and another therapeutic agent useful in the treatment of HIV infection, such as a component used for HAART or immunotoxins.

As noted above, compositions described herein may be combined with one or more additional therapeutic agents useful in the treatment of HIV infection. It will be understood that the scope of combinations of the compounds of this invention with HIV/AIDS antivirals, immunomodulators, anti-infectives or vaccines is not limited to the following list, and includes in principle any combination with any pharmaceutical composition useful for the treatment of AIDS. The HIV/AIDS antivirals and other agents will typically be employed in these combinations in their conventional dosage ranges and regimens as reported in the art.

Examples of antiviral agents include (but not restricted) ANTIVIRALS Manufacturer (Tradename and/or Drug Name Location) Indication (Activity): abacavir GlaxoSmithKline HIV infection, AIDS, ARC GW 1592 (ZIAGEN) (nRTI); 1592U89 abacavir+GlaxoSmithKline HIV infection, AIDS, ARC (nnRTI); lamivudine+(TRIZIVIR) zidovudine acemannan Carrington Labs ARC (Irving, Tex.) ACH 126443 Achillion Pharm. HIV infections, AIDS, ARC (nucleoside reverse transcriptase inhibitor); acyclovir Burroughs Wellcome HIV infection, AIDS, ARC, in combination with AZT AD-439 Tanox Biosystems HIV infection, AIDS, ARC AD-519 Tanox Biosystems HIV infection, AIDS, ARC adefovir dipivoxil Gilead HIV infection, AIDS, ARC GS 840 (RTI); AL-721 Ethigen ARC, PGL, HIV positive, (Los Angeles, Calif.), AIDS alpha interferon GlaxoSmithKline Kaposi's sarcoma, HIV, in combination w/Retrovir AMD3100 AnorMed HIV infection, AIDS, ARC (CXCR4 antagonist); amprenavir GlaxoSmithKline HIV infection, AIDS, 141 W94 (AGENERASE) ARC (PI); GW 141 VX478 (Vertex) ansamycin Adria Laboratories ARC LM 427 (Dublin, Ohio) Erbamont (Stamford, Conn.) antibody which neutralizes; Advanced Biotherapy AIDS, ARC pH labile alpha aberrant Concepts (Rockville, Interferon Md.) AR177 Aronex Pharm HIV infection, AIDS, ARC atazanavir (BMS 232632) Bristol-Myers-Squibb HIV infection, AIDS, ARC (ZRIVADA) (PI); beta-fluoro-ddA Nat'l Cancer Institute AIDS-associated diseases BMS-232623 Bristol-Myers Squibb/HIV infection, AIDS, (CGP-73547) Novartis ARC (PI); BMS-234475 Bristol-Myers Squibb/ HIV infection, AIDS, (CGP-61755) Novartis ARC (PI); capravirine Pfizer HIV infection, AIDS, (AG-1549, S-1153) ARC (nnRTI); CI-1012 Warner-Lambert HIV-1 infection cidofovir Gilead Science CMV retinitis, herpes, papillomavirus curdlan sulfate AJI Pharma USA HIV infection cytomegalovirus immune MedImmune CMV retinitis globin cytovene Syntex sight threatening CMV ganciclovir peripheral CMV retinitis delavirdine Pharmacia-Upjohn HIV infection, AIDS, (RESCRIPTOR) ARC (nnRTI); dextran Sulfate Ueno Fine Chem. Ind. AIDS, ARC, HIV Ltd. (Osaka, Japan) positive asymptomatic ddC Hoffman-La Roche HIV infection, AIDS, ARC (zalcitabine, (HIVID) (nRTI); dideoxycytidine ddI Bristol-Myers Squibb HIV infection, AIDS, ARC; Dideoxyinosine (VIDEX) combination with AZT/d4T (nRTI) DPC 681 & DPC 684 DuPont HIV infection, AIDS, ARC (PI) DPC 961 & DPC 083 DuPont HIV infection AIDS, ARC (nnRTRI); emvirine Triangle Pharmaceuticals HIV infection, AIDS, ARC (CO-ACTINON) (non-nucleoside reverse transcriptase inhibitor); EL10 Elan Corp, PLC HIV infection (Gainesville, Ga.) efavirenz DuPont HIV infection, AIDS, (DMP 266) (SUSTIVA) ARC (nnRTI); Merck (STOCRIN) famciclovir Smith Kline herpes zoster, herpes simplex emtricitabine Triangle Pharmaceuticals HIV infection, AIDS, ARC FTC (CO-VIRACIL) (nRTI); Emory University emvirine Triangle Pharmaceuticals HIV infection, AIDS, ARC (COACTI-NON) (non-nucleoside reverse transcriptase inhibitor); HBY097 Hoechst Marion Roussel HIV infection, AIDS, ARC (nnRTI); hypericin VIMRx Pharm. HIV infection, AIDS, ARC recombinant human; Triton Biosciences AIDS, Kaposi's sarcoma, interferon beta (Almeda, Calif.); ARC interferon alfa-n3 Interferon Sciences ARC, AIDS indinavir; Merck (CRIXIVAN) HIV infection, AIDS, ARC, asymptomatic HIV positive, also in combination with AZT/ddI/ddC (PI); ISIS 2922 ISIS Pharmaceuticals CMV retinitis JE2147/AG1776; Agouron HIV infection, AIDS, ARC (PI); KNI-272 Nat'l Cancer Institute HIV-assoc. diseases lamivudine; 3TC Glaxo Wellcome HIV infection, AIDS, (EPI-VIR) ARC; also with AZT (nRTI); lobucavir Bristol-Myers Squibb CMV infection; lopinavir (ABT-378) Abbott HIV infection, AIDS, ARC (PI); lopinavir+ritonavir Abbott (KALETRA) HIV infection, AIDS, ARC (ABT-378/r) (PI); mozenavir AVID (Camden, N.J.) HIV infection, AIDS, ARC (DMP-450) (PI); nelfinavir Agouron HIV infection, AIDS, (VIRACEPT) ARC (PI); nevirapine Boeheringer HIV infection, AIDS, Ingleheim ARC (nnRTI); (VIRAMUNE) novapren Novaferon Labs, Inc. HIV inhibitor (Akron, Ohio); pentafusaide Trimeris HIV infection, AIDS, ARC T-20 (fusion inhibitor); peptide T Peninsula Labs AIDS octapeptide (Belmont, Calif.) sequence PRO 542 Progenics HIV infection, AIDS, ARC (attachment inhibitor); PRO 140 Progenics HIV infection, AIDS, ARC (CCR5 co-receptor inhibitor); trisodium Astra Pharm. Products, CMV retinitis, HIV infection, phosphonoformate Inc other CMV infections; PNU-140690 Pharmacia Upjohn HIV infection, AIDS, ARC (PI); probucol Vyrex HIV infection, AIDS; RBC-CD4Sheffield Med. Tech HIV infection, AIDS, (Houston Tex.) ARC; ritonavir Abbott HIV infection, AIDS, (ABT-538) (RITONAVIR) ARC (PI); saquinavir Hoffmann-LaRoche HIV infection, AIDS, (FORTOVASE) ARC (PI); stavudine d4T Bristol-Myers Squibb HIV infection, AIDS, ARC didehydrodeoxy-(ZERIT.) (nRTI); thymidine T-1249 Trimeris HIV infection, AIDS, ARC (fusion inhibitor); TAK-779 Takeda HIV infection, AIDS, ARC (injectable CCR5 receptor antagonist); tenofovir Gilead (VIREAD) HIV infection, AIDS, ARC (nRTI); tipranavir (PNU-140690) Boehringer Ingelheim HIV infection, AIDS, ARC (PI); TMC-120 & TMC-125 Tibotec HIV infections, AIDS, ARC (nnRTI); TMC-126 Tibotec HIV infection, AIDS, ARC (PI); valaciclovir GlaxoSmithKline genital HSV & CMV infections virazole Viratek/ICN (Costa asymptomatic HIV positive, ribavirin Mesa, Calif.) LAS, ARC; zidovudine; AZT GlaxoSmithKline HIV infection, AIDS, ARC, (RETROVIR) Kaposi's sarcoma in combination with other therapies (nRTI); [PI=protease inhibitor nnRTI=non-nucleoside reverse transcriptase inhibitor NRTI=nucleoside reverse transcriptase inhibitor].

The additional therapeutic agent may be used individually, sequentially, or in combination with one or more other such therapeutic agents described herein (e.g., a reverse transcriptase inhibitor used for HAART, a protease inhibitor used for HAART, an HIV-1 protein derived from the subject and/or an activator of latent HIV expression). Administration to a subject may be by the same or different route of administration or together in the same pharmaceutical formulation.

According to this embodiment, a composition comprising HIV-1 protein derived from the subject and an activator of latent HIV expression may be coadministered with any HAART regimen or component thereof. The current standard of care using HAART is usually a combination of at least three nucleoside reverse transcriptase inhibitors and frequently includes a protease inhibitor, or alternatively a non-nucleoside reverse transcriptase inhibitor. Subjects who have low $CD4^+$ cell counts or high plasma RNA levels may require more aggressive HAART. For subjects with relatively normal $CD4^+$ cell counts and low to non-measurable levels of plasma HIV RNA over prolonged periods (i.e., slow or non-progressors) may require less aggressive HAART. For antiretroviral-naive subject who are treated with initial antiretroviral regimen, different combinations (or cocktails) of antiretroviral drugs can be used.

Thus, in some embodiments, a pharmaceutical composition comprising an HIV-1 protein derived from the subject and an activator of latent HIV expression may be coadministered to the subject with a "cocktail" of nucleoside reverse transcriptase inhibitors, non-nucleoside HIV reverse transcriptase inhibitors, and protease inhibitors. For example, a pharmaceutical composition including an HIV-1 protein derived from the subject as described herein and an HDAC inhibitor may be coadministered with a cocktail of two nucleoside reverse transcriptase inhibitors (e g , ZIDOVUDINE (AZT) and LAMIVUDINE (3TC)), and one protease inhibitor (e.g., INDINAVIR (MK-639)). A pharmaceutical composition including an HIV-1 protein derived from the subject and an activator of latent HIV expression, such as an HDAC inhibitor, may also be coadministered to the subject with a cocktail of one nucleoside reverse transcriptase inhibitor (e.g., STAVUDINE (d4T)), one non-nucleoside reverse transcriptase inhibitor (e.g., NEVIRAPINE (BI-RG-587)), and one protease inhibitor (e.g., NELFINAVIR (AG-1343)). Alternatively, a composition comprising an HIV-1 protein derived from the subject and an HDAC inhibitor may be coadministered to the subject with a cocktail of one nucleoside reverse transcriptase inhibitor (e.g., ZIDOVUDINE (AZT)), and two protease inhibitors (e.g., NELFINAVIR (AG-1343) and SAQINAVIR (Ro-31-8959)).

Coadministration in the context of this invention is defined to mean the administration of more than one therapeutic agent in the course of a coordinated treatment to achieve an improved clinical outcome. Such coadministration may also be coextensive, that is, occurring during overlapping periods of time.

This regimen may be continued for a period past the point when the levels of integrated and unintegrated HIV in active and HIV-specific memory T cells are undetectably low. At the end of the period, the subject is weaned from HAART and from the HIV-1 protein derived from the subject and/or activators of latent HIV expression. At this point, the subject is monitored for reestablishment of normal immune function and for signs of reemergence of HIV infection. Additionally, any needed conjunctive immunotherapy, such as bone marrow transplants, various cytokines or vaccination, may be administered. After this, the subject is monitored on a routine basis for life to detect reemergence of HIV infection, in which case repeat therapy according to the above embodiments may be performed.

In additional embodiments, immunotoxins may be employed in a method of the present invention. In some embodiments, the administration of an HIV-1 protein derived from the subject can render a subject's cells having an integrated HIV genome sensitive to an immunotoxin. In some embodiments, an immunotoxin can be coadministrered to a subject with HIV-1 protein derived from the subject and activators of latent HIV expression. An exemplary immunotoxin is an immunotoxin targeted to an HIV protein expressed on the exterior of cells, such as the viral envelope glycoprotein or a portion thereof. The term "immunotoxin" refers to a covalent or non-covalent linkage of a toxin to an antibody, such as an anti HIV envelope glycoprotein antibody. The toxin may be linked directly to the antibody, or indirectly through, for example, a linker molecule. The toxin can be selected from the group consisting of ricin-A and abrin-A.

Activation of latent HIV expression (also referred to as reactivation of latent HIV expression) results in the conversion of latently infected cells to productively infected cells. This transition can be measured by any characteristic of active viral infection, e.g., production of infectious particles, reverse transcriptase activity, secreted antigens, cell-surface antigens, soluble antigens, HIV RNA and HIV DNA, etc. The methods described herein, may optionally include the step of determining or detecting activation of latent HIV expression. In one embodiment, such a method comprises determining or detecting an mRNA, e.g., an HIV mRNA. Other mRNAs, such as Tat mRNA, NF-κB mRNA, NF-AT mRNA and other mRNAs encoding polypeptides can also be determined using the well known methods including but not limited to hybridization and amplification based assays.

In another embodiment, amplification-based assays are used to measure the expression level of an HIV gene. In one embodiment, activation of latent HIV expression can be detecting by determining the expression level of an HIV polypeptide. The expression level of an HIV polypeptide may be determined by several methods, including, but not limited to, affinity capture, mass spectrometry, traditional immunoassays directed to HIV proteins (such as gp120 and reverse transcriptase), PAGE, Western Blotting, or HPLC as further described herein or as known by one of skill in the art.

Detection paradigms that can be employed to this end include optical methods, electrochemical methods (voltammetry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

In some embodiments, global sequencing and 454 pyrosequensing of vaccine constructs and the PCR products described herein can be performed to confirm the production and purity of an autologous virus population. 454 is a simple, efficient, and cost effective means to obtain approximate genetic diversity in the samples. In an exemplary embodiment, DNA vectors and plasma RNA will be amplified with bar-coded primers and then sequenced using a 454 JR to obtain an average of ~2000 reads per amplicon/sample.

Pharmaceutical compositions described herein can be formulated by standard techniques using one or more physiologically acceptable carriers or excipients. Suitable pharmaceutical carriers are described herein and in "Remington's Pharmaceutical Sciences" by E. W. Martin. The small molecule compounds of the present invention and their physiologically acceptable salts and solvates can be formulated for administration by any suitable route, including via inhalation, topically, nasally, orally, parenterally, or rectally. Thus, the administration of the pharmaceutical composition may be made by intradermal, subdermal, intravenous, intramuscular, intranasal, intracerebral, intratracheal, intraarterial, intraperitoneal, intravesical, intrapleural, intracoronary or intratumoral injection, with a syringe or other devices. Transdermal administration is also contemplated, as are inhalation or aerosol administration. Tablets and capsules can be administered orally, rectally or vaginally.

For oral administration, a pharmaceutical composition or a medicament can take the form of, for example, a tablets or a capsule prepared by conventional means with a pharmaceutically acceptable excipient. Preferred are tablets and gelatin capsules comprising the active ingredient, i.e., a small molecule compound of the present invention, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate; (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

Compounds described herein can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient.

For administration by inhalation, the compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

Suitable formulations for transdermal application include an effective amount of a compound of the present invention with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The compounds can also be formulated in rectal compositions, for example, suppositories or retention enemas, for example, containing conventional suppository bases, for example, cocoa butter or other glycerides.

Furthermore, the compounds can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

In one embodiment, a pharmaceutical composition is administered to a subject, preferably a human, at a therapeutically effective dose to prevent, treat, or control a condition or disease as described herein, such as HIV latency.

The dosage of active compounds administered is dependent on the species of warm-blooded animal (mammal), the body weight, age, individual condition, surface area of the area to be treated and on the form of administration. The size of the dose also will be determined by the existence, nature, and extent of any adverse effects that accompany the administration of a particular small molecule compound in a particular subject. Typically, a dosage of the active compounds of the present invention is a dosage that is sufficient to achieve the desired effect. Optimal dosing schedules can be calculated from measurements of compound accumulation in the body of a subject. In general, dosage may be given once or more daily, weekly, or monthly. Persons of ordinary skill in the art can easily determine optimum dosages, dosing methodologies and repetition rates.

In another embodiment, a pharmaceutical composition including HIV-1 protein derived from the subject is administered in a daily dose in the range from about 0.1 mg per kg of subject weight (0.1 mg/kg) to about 1 g/kg for multiple days. In another embodiment, the daily dose is a dose in the range of about 5 mg/kg to about 500 mg/kg. In yet another embodiment, the daily dose is about 10 mg/kg to about 250 mg/kg. In yet another embodiment, the daily dose is about 25 mg/kg to about 150 mg/kg. A preferred dose is about 10 mg/kg. The daily dose can be administered once per day or divided into subdoses and administered in multiple doses, e.g., twice, three times, or four times per day. However, as will be appreciated by a skilled artisan, activators of latent HIV expression and one or more HIV-1 coding sequences derived from a subject may be administered in different amounts and at different times.

To achieve the desired therapeutic effect, compositions described herein may be administered for multiple days at the therapeutically effective daily dose. Thus, therapeutically effective administration of compounds to treat a condition or disease described herein in a subject requires periodic (e.g., daily) administration that continues for a period ranging from three days to two weeks or longer. Typically, compounds will be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the compounds are not administered daily, so long as the administration is repeated frequently enough to maintain a therapeutically effective concentration of the compounds in the subject. For example, one can administer the compounds every other day, every third day, or, if higher dose ranges are employed and tolerated by the subject, once a week. A preferred dosing schedule, for example, is administering daily for a week, one week off and repeating this cycle dosing schedule for 3-4 cycles.

Optimum dosages, toxicity, and therapeutic efficacy of such compounds may vary depending on the relative potency of individual compounds and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Compounds that exhibit large therapeutic indices are preferred. While compounds that exhibit toxic side effects can be used, care should be taken to design a delivery system that targets such compounds to the HIV infected cells to minimize potential damage to normal cells and, thereby, reduce side effects. In addition, combinations of compounds having synergistic effects described herein can be used to further reduce toxic side effects of one or more agents comprising a pharmaceutical composition of the invention.

The data obtained from, for example, cell culture assays and animal studies can be used to formulate a dosage range for use in humans. The dosage of such small molecule compounds lies preferably within a range of circulating concentrations that include the $ED_{50}$ with little or no toxicity. The dosage can vary within this range depending upon the dosage form employed and the route of administration. For any compounds used in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of compounds is from about 1 ng/kg to 100 mg/kg for a typical subject.

Following successful treatment, it may be desirable to have the subject undergo maintenance therapy to prevent the recurrence of the condition or disease treated.

Although the forgoing invention has been described in some detail by way of illustration and example for clarity and understanding, it will be readily apparent to one ordinary skill in the art in light of the teachings of this invention that certain variations, changes, modifications and substitution of equivalents may be made thereto without necessarily departing from the spirit and scope of this invention. As a result, the embodiments described herein are subject to various modifications, changes and the like, with the scope of this invention being determined solely by reference to the claims appended hereto. Those of skill in the art will readily recognize a variety of non-critical parameters that could be changed, altered or modified to yield essentially similar results.

The referenced patents, patent applications, and scientific literature, including accession numbers to GenBank database sequences, referred to herein are hereby incorporated by reference in their entirety as if each individual publication, patent or patent application were specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As can be appreciated from the disclosure above, the present invention has a wide variety of applications. The invention is further illustrated by the following examples, which are only illustrative and are not intended to limit the definition and scope of the invention in any way.

EXAMPLE 1

Yeast Based HIV-1 Cloning System

Figure 3:
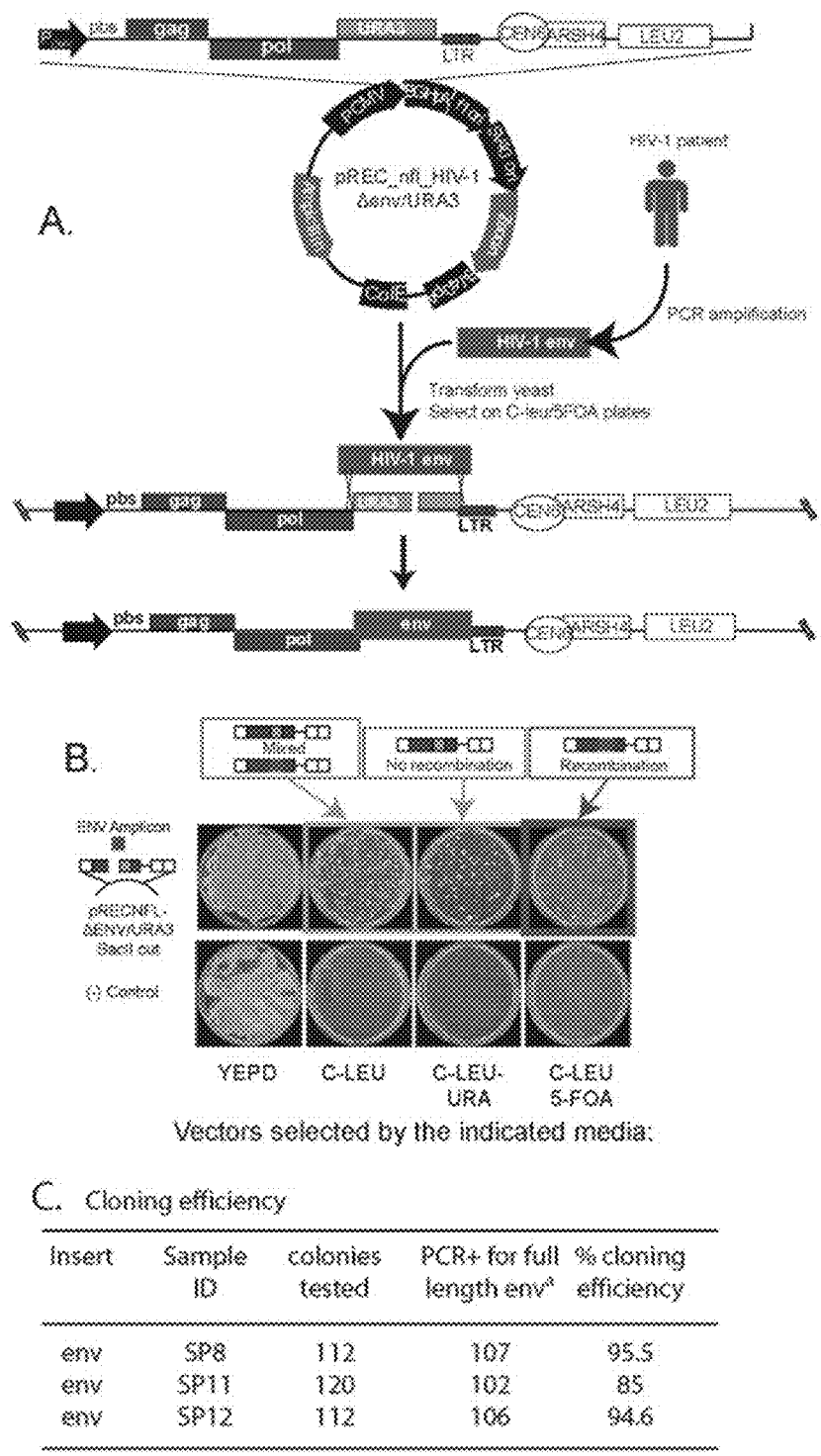

A universal HIV-1 cloning vector, pREC_nfl_HIV-1Δproteome/URA3 was constructed where the URA3 gene replaces the entire HIV-1 coding sequence. Details of this system are described in FIG. 3A. To insert the full HIV-1 coding region, the HIV-1 genome is transformed with pREC_nfl_HIV-1Δproteome/URA3 vector into a specific *S cerevisiae* strain (FIGS. 3 A and B) then grown of FOA+/leu-plates. FOA is converted into the toxic anabolite unless URA3 is replaced by HIV-1 DNA genome via homologous recombination/gap repair (FIGS. 3B and C). This system has several advantages over existing technology:

(1) One step insertion of a large PCR amplicon into a vector.

(2) URA3 negative selectable system ensures that 98% of colonies contain the correct, in-frame insert (3) Efficiency of yeast recombination is such that recombination between one PCR product and vector yields >10,000 FOA resistant colonies This cloning system is the technological backbone for our ACT-VEC preparation. Our pREC HIV-1 nfl plasmid upon 293T transfections produces vectors that:

(1) lack 5'LTR and as such, cannot initiate reverse transcription (FIG. 3A)

Figure 4:
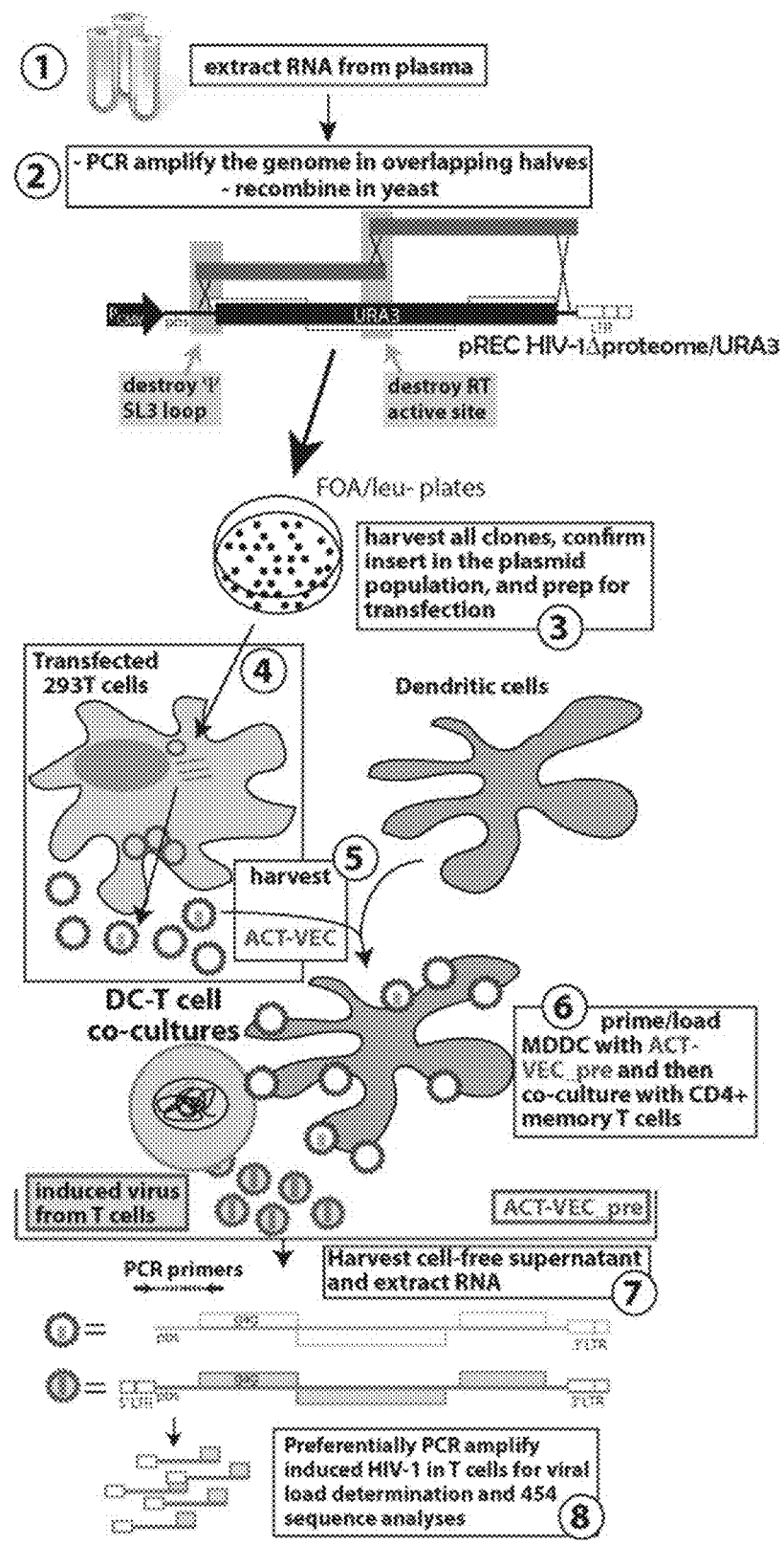

(2) lack a functional reverse transcriptase enzyme (FIG. 4)

(3) lack genomic RNA due to deletion of w packaging element (FIG. 4)

Figure 5:
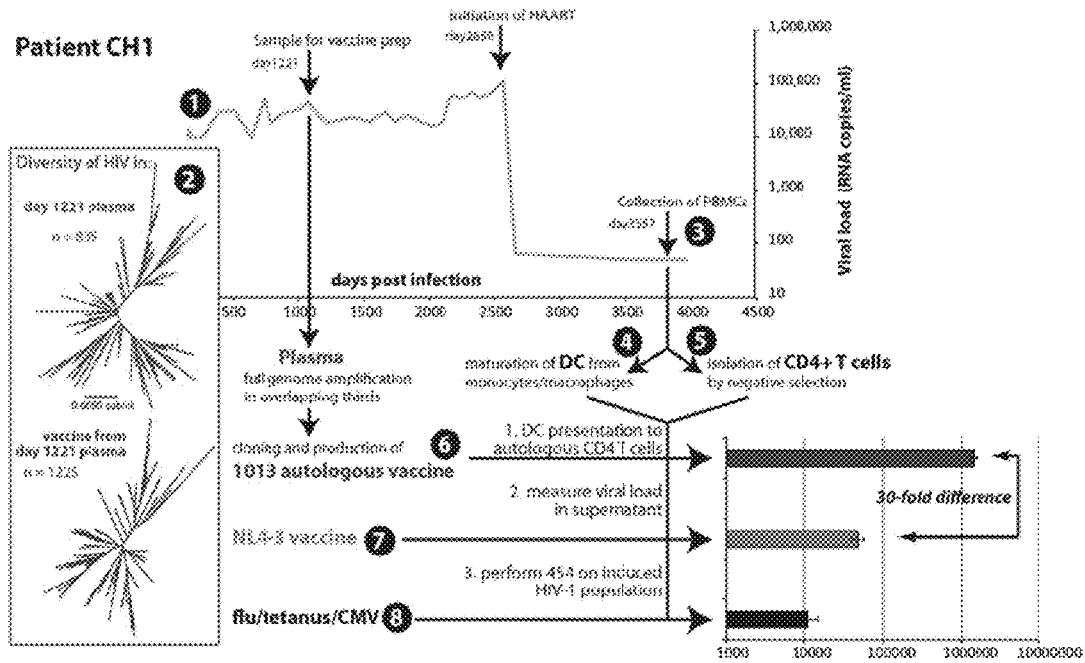
Figure 6:
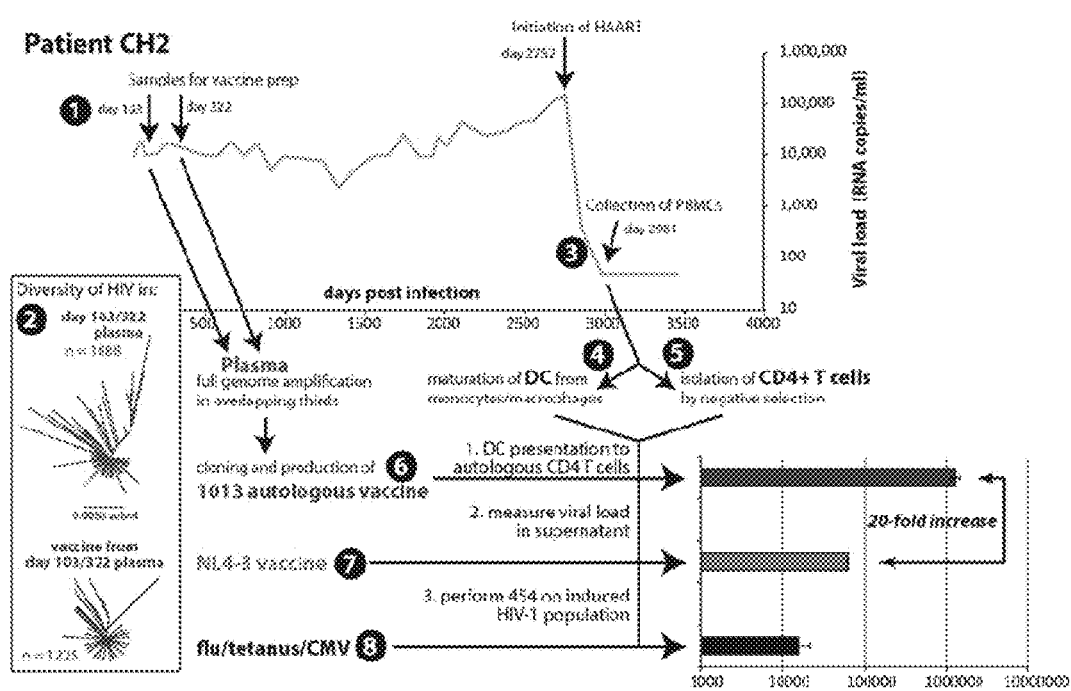
Figure 7:
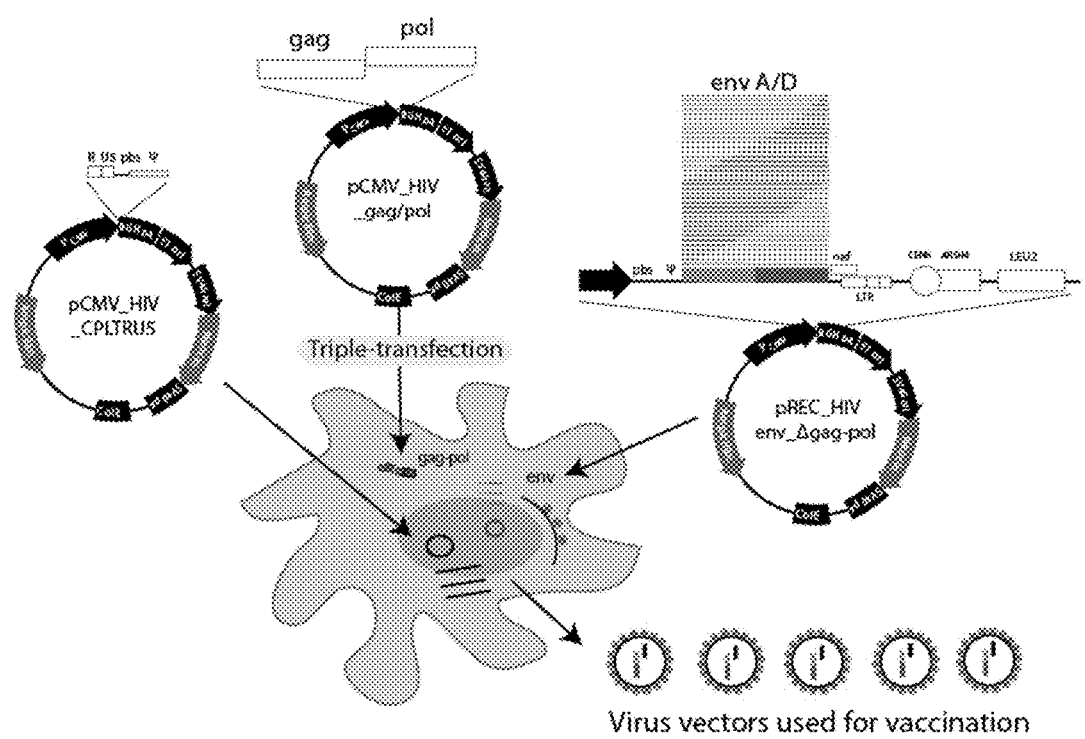

(4) contains full complement of HIV-1 proteins in the correct stoichmetry (5) are dead but morphologically identical to wildtype Autologous, Multivalent ACT-VEC can Activate HIV-specific CD4+ T Cells to Produce Virus The protocol for ACT-VEC production and testing is described in FIGS. 4, 5 and 6. Preliminary studies are from two patients on stable first line HAART with available samples prior to HAART initiation. Plasma samples were obtained at day1221 post-infection for patient CH1 and days 103& 322 for patient CH2 (FIGS. 5 and 6). Viral RNA was RT-PCR amplified into two overlapping HIV DNA products (FIG. 4) which deleted ψ and RT active site (FIG. 4). The two HIV-1 products were recombined into pREC_nfl_HIV-1Δproteome/URA3 as described above. Approximately 1000 colonies were scraped from the FOA/leu-150 mm petri dish for plasmid purification. A large scale plasmid transfection was performed on 293T cells and ACT-VEC_pre was harvested at 72 h.

In order to determine HIV genetic diversity, RNA from ACT-VEC_pre and from plasma sample were subject to RT-PCR with a set of barcoded 454 primers to amplify a 500 bp PBS-gagMA fragment, which was then sequenced using a Roche 454Jr instrument. As previously described, we have developed software pipelines to "bin" sequence based on barcodes, align, and then construct trees using maximum-likelihood analyses through MEGA and Treemap. As indicated in FIGS. 5 and 6, we observed similar genetic diversity in HIV-1 within plasma (RT-PCR amplified) as compared to that found in ACT-VEC_pre. These findings suggest that we are accurately sampling and producing a full-length HIV-1 vaccine based on the HIV-1 population (at a given time point in disease). It is important to note that HIV-1 genetic diversity in CH1 plasma and in ACT-VEC_pre$_{CH1}$ was much greater than that from patient CH2 (compare FIG. 5 and FIG. 6). This was expected considering extensive virus evolution occurs over 3 years of infection (i.e., time separating sampling in CH1 and CH2) (FIGS. 5 and 6).

Cryopreserved PBMCs were available from CH1 at day 3557, i.e. ~2.5yrs following initiation of HAART and ~6.4yrs since sample for ACT-VEC_pre$_{CH1}$ preparation (FIG. 5). A similar PBMC samples was available from CH2 at day 2981 (FIG. 6). Monocyte derived dendritic cells (MDDC) and CD4+ memory T cells were obtained from two PBMC aliquots using standard methods (FIGS. 5 and 6). MDDC ($5 \times 10^4$/well,FIG. 4) were then incubated with either:

the ACT-VEC_pre prep a mixture of influenza M1/tetanus toxoid/CMVpp65 a vaccine prep derived from NL4-3 (FIGS. 5 and 6)

Antigen-loaded MDDC were then incubated with autologous memory/CD4+ T cells ($10^6$ cells):

to stimulate virus production in the memory-CD4+ T cells or, to measure activation via y-inteferon ELISPOT Although the Ψ element was deleted, any HIV RNA packaged in ACT-VEC_pre would be indistinguishable from the activated HIV-1 from memory T cells. Since our pRE- C_nfl_HIV-1$_{ACT-VEC}$ lacks the 5'LTR, we designed a set of real-time PCR primers with one primer and the fluorescent probe in the U5 region such that only virus from activated T cells would be quantified (and not from ACT-VEC_pre; FIG. 4). With patient CH1 (FIG. 5), HIV-1 production from CD4+ T cells was 30-fold higher with ACT-VEC_pre than with NL4-3 vaccine, both presented by MDDC; and 128-fold higher than with flu/tetanus/CMV antigens. With patient CH2 (FIG. 6), the differences in HIV-1 production from T cells were 20 and 83-fold higher, respectively. These findings suggest that equal quantities of autologous ACT-VEC_pre was much more effective than clonal ACT-VEC_NL4-3 at activating virus production from CD4+/memory T cells.

Using ELISPOT, flu/tetanus/CMV antigen cocktail was much more efficient at activating T cells via DC presentation (161 spot forming units/$10^6$ cells or sfu) than either autologous or NL4-3 vectors (<10 sfu). The same was observed with CH2. This was in sharp contrast to the higher levels of HIV-1 production observed with autologous vectors.

These findings suggest that in these two patients, latent HIV-1 is more frequently found in HIV-specific memory T cells rather than in Flu/TT/CMV-specific memory T cells. Thus, activated HIV-specific CD4 T cells were likely in greater abundance than other activated CD4+ T cells during early HIV infection and prior to treatment (FIG. 1).

EXAMPLE 2

Our team will perform both human ex vivo analyses and macaque vaccinations to evaluate the best therapeutic HIV-1 vaccine to activate the specific memory T cell population latently infected with HIV-1. We will focus on the use of autologous, multivalent HIV-1 vaccine vectors constructed from the infecting virus prior to HAART or the latent HIV-1 found in the memory T cells during stable HAART. In most primary HIV-1 infections, a single HIV-1 clone is successfully transmitted from recipient to donor to establish a new infection. This clone is then the evolutionary template (or founder virus) for the HIV-1 population that continues to diversify in the absence of treatment within the patient.

To test if this single clone contains the hallmark feature for a successful therapeutic vaccine, we will also construct a vaccine based on the autologous consensus HIV-1 clone found at early infection. To determine if the HIV-1 heterogeneity of the immunogen is more important than the high degree of similarity to the host virus, we have constructed heterogenous subtype B vaccine utilizing the same vector vehicle. We will produce and test preventative vaccines based on multivalent vaccine vectors. We have adopted recombination between divergent subtype B HIV-1 isolates to diversify and clone functional HIV-1 genes/coding regions. These multivalent vaccines can be controlled to contain as few as 10 to greater than 1,000 unique variants where the recombination breakpoints in a quarter of the variant occurs within a codon to generate a nonsynonymous but functional amino acid substitution. The degree of functional heterogeneity of this heterologous subtype B vaccine can be designed to be greater than in the autologous, heterogeneous HIV-1 vaccine (vaccine B). We would hope that this diversity of the heterologous vaccine would be sufficient as a therapeutic vaccine. However, based on specificity of immune escape in autologous virus and ensuing, altered response in the host, we suspect that very specific and directed autologous vaccines would be best to activate the HIV-specific resting memory CD4+ T cells harboring the latent HIV-1 in patients receiving HAART and with undetectable virus levels. When these cells are activated, any latent HIV-1 would be induced to replicate but also, these cells would then be programmed for death by apoptosis, necrosis or perhaps even elimination by another T cell (i.e., HIV-specific CTLs).

It is important to note that the term "vaccine" in this example is misleading. Although these autologous vaccines may induce a de novo HIV-specific response from naïve T and B cells, our intended goal is primarily to stimulate those HIV-specific resting memory CD4+ T cells that were initially activated in early disease and prior to HAART. Activation of the HIV-specific memory T cells by this vaccine would also stimulate replication of latent virus and ultimately lead to cell death. The virus produced from these cells would then be inhibited via presence of the three antiretroviral drugs. Again, we suspect that the vast majority of naïve T cells were activated HIV-1 antigens during early infection and that the immune response was overwhelmed by these HIV-specific antigens. Although T cells may also have been activated to other non-HIV-1 antigens during early disease, the high proportion of HIV-specific T cells over other antigen-specific T cells suggests that HIV-1 infection/replication/evolution may have predominated in the HIV-specific, activated T cells in early disease.

To test this hypothesis, we have developed a strategy to compare the activation of memory T cells and induction of latent HIV-1 using human DCs and T cells ex vivo. We will add the various autologous HIV-1 vaccines, the heterologous subtype B HIV-1 vaccine, as well as various recall antigens (tetanus, CMV, flu) to the autologous DCs to then present these antigens to the memory T cell subset from the autologous HAART patient. We will measure T cell activation as well as the production of virus. More importantly, we will analyze the diversity of the HIV-1 population that is stimulated to replicate in the T cells and compare, by phylogenetic analyses, this ex vivo activated HIV-1 population to the HIV-1 populations found in the patient prior to HAART and within the memory T cells during stable HAART. A match in the number of specific HIV-1 clones in the ex vivo stimulated virus population to that found in the memory T cells during HAART would suggest an efficient activation of the latent HIV-1 in this cell population. We will perform these same phylogenetic comparisons on the ex vivo virus population after stimulation of memory T cells with various recall antigens and with mitogen stimulation. We suspect that mitogen stimulation will induce a diverse HIV-1 population only slightly more representative to the latent HIV-1 pool than the autologous, multivalent HIV-1 vaccines. However, only minimal amounts of virus with a limited genetic diversity should be activated by the various recall antigens. These findings would suggest that HIV-specific T cells are more numerous and more readily infected that other antigen-specific T cells in early disease.

Thus far, we have described the autologous HIV-1 vaccines to be tested ex vivo. We will carry out these "test-of-concept" studies on a SIV/Chinese rhesus macaque (Ch RM) model. This model is considered to be unique in that it most closely mimics HIV-1 infection in comparison with any other non-human primate (NHP) models. It has been widely used for HIV-1 pathogenesis and increasingly used for vaccine studies. The rationale of the proposal and the strategy of the autologous SIV-based vaccine design will be similar to that of anti-HIV autologus vaccines (i.e., Vaccine A and Vaccine B). Moreover, we will take advantage of this model that: a) we can access to blood and tissues (here mainly focuses on the gut) longitudinally, so we will gain a clear picture of overall kinetics of viral diversity and evolution in different compartments for optimal vaccine design; b) we can control for viral inoculum, route, dose, timing of infection, administer essentially unlimited cART; and furthermore c) we will test effectiveness of vaccines in vivo.

In addition, we will identify twenty HIV-1 infected patients receiving first line HAART for 2-4 years with no rebounds in viral load. Patients must have been sampled for a minimum of 2 years prior to first line HAART and these samples must be available through the Clinical Core at the CWRU Center for AIDS Research. We will also attempt to select patients with known infection dates and with sample availability within the first six months of infection. When considering these inclusion/exclusion criteria and our ability to PCR amplify the HIV-1 genes, we anticipate a cohort of ten patients. These stable HIV-infected patients receiving HAART must be willing to have at least one large volume (500 ml) blood draw.

The methodology of processing patient samples includes PCR amplifying the gag/pol and env genes from:

a. Sample within six months of infection (vaccine A)

b. Samples from early infection until the initiation of HAART (vaccine B)

c. A minimum of 5 DNA aliquots of $10^6$ memory T cells from each patient (vaccine C)

It is important to note that we can clone with two or three PCR products for each replacement cassette. URA3 gene will be replaced by the gag/pol amplicon (one or two overlapping PCR fragment) in pRECnfl-Δgag-pol/URA3 homologous recombination/gap repair in yeast and then replace the URA3 gene by the env amplicon (one or two overlapping PCR fragment) by homologous recombination/ gap repair in yeast. We can then transfect pREC_EXP_gag/ pol, pREC_SIN_env, and pCMV_cplt into 293T cells to produce vaccine constructs A, B, and C from a minimum of ten patients. We can also obtain heterogeneous subtype B gag/pol and env cassettes from RO1 AI084816 for vaccine construct D.

454 pyrosequencing and sequence analyses of vaccine constructs A, B, and C will be performed from samples derived from each of the ten patients and of vaccine D as well as the original PCR products from each of the ten patients. Phylogenetic analyses will be used to compare the HIV-1 sequences sampled prior to HAART, any genetic bottlenecks in the vaccine constructs (B and C only), and to determine the representation of the autologous intrapatient population in the vaccines in the memory T cell population during HAART.

DCs and CD4+ memory T cells from leukocytes obtained from a large volume blood draw can then be separated and DCs incubated with the various autologous vaccine preps (A, B, and C), the heterologous vaccine D, tetanus toxin, and CMV. Then "loaded" or untreated DCs are to be co-incubated with the autologous memory CD4+ T cells and the level of T cell activation can then be measured by IFN-gamma ELISPOT and intracytoplasmic flow cytometry. Finally, the amount of HIV-1 replication/release by RT activity will be measured.

Figure 8:
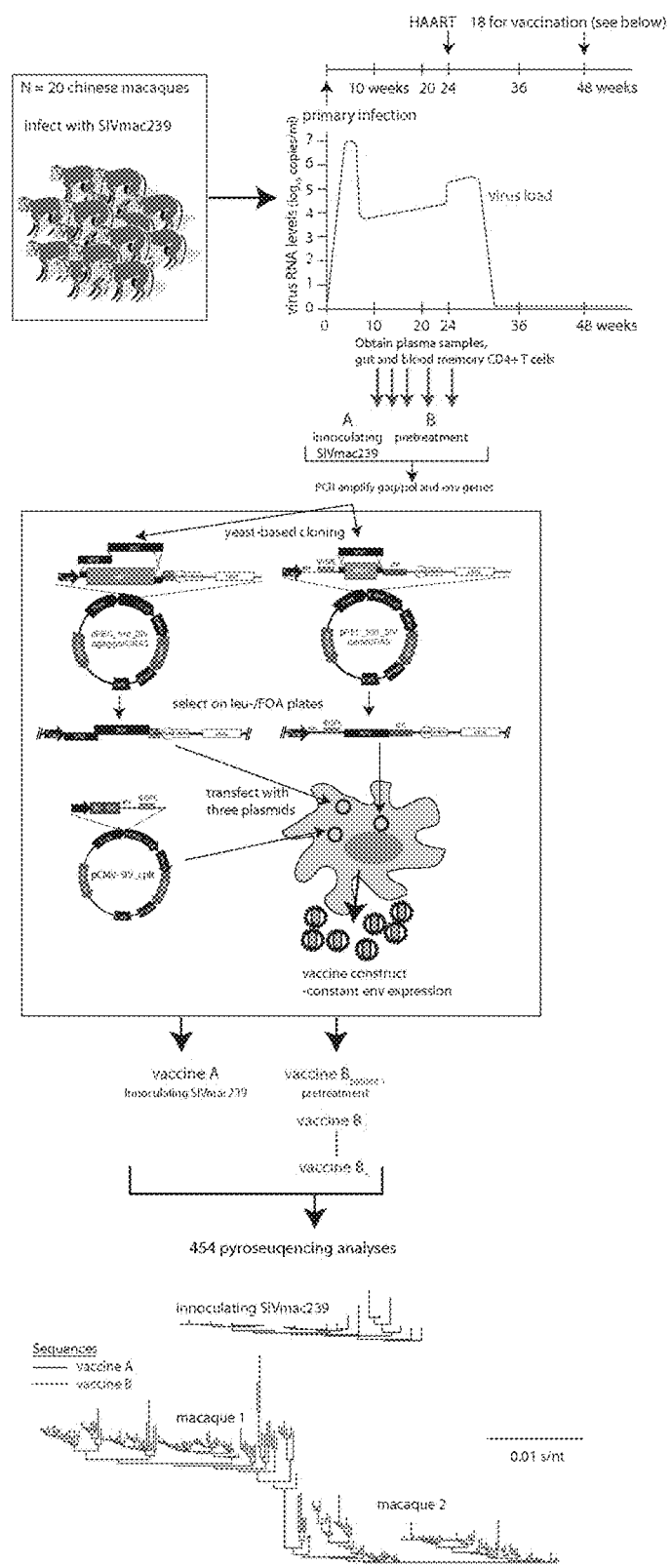
Figure 9:
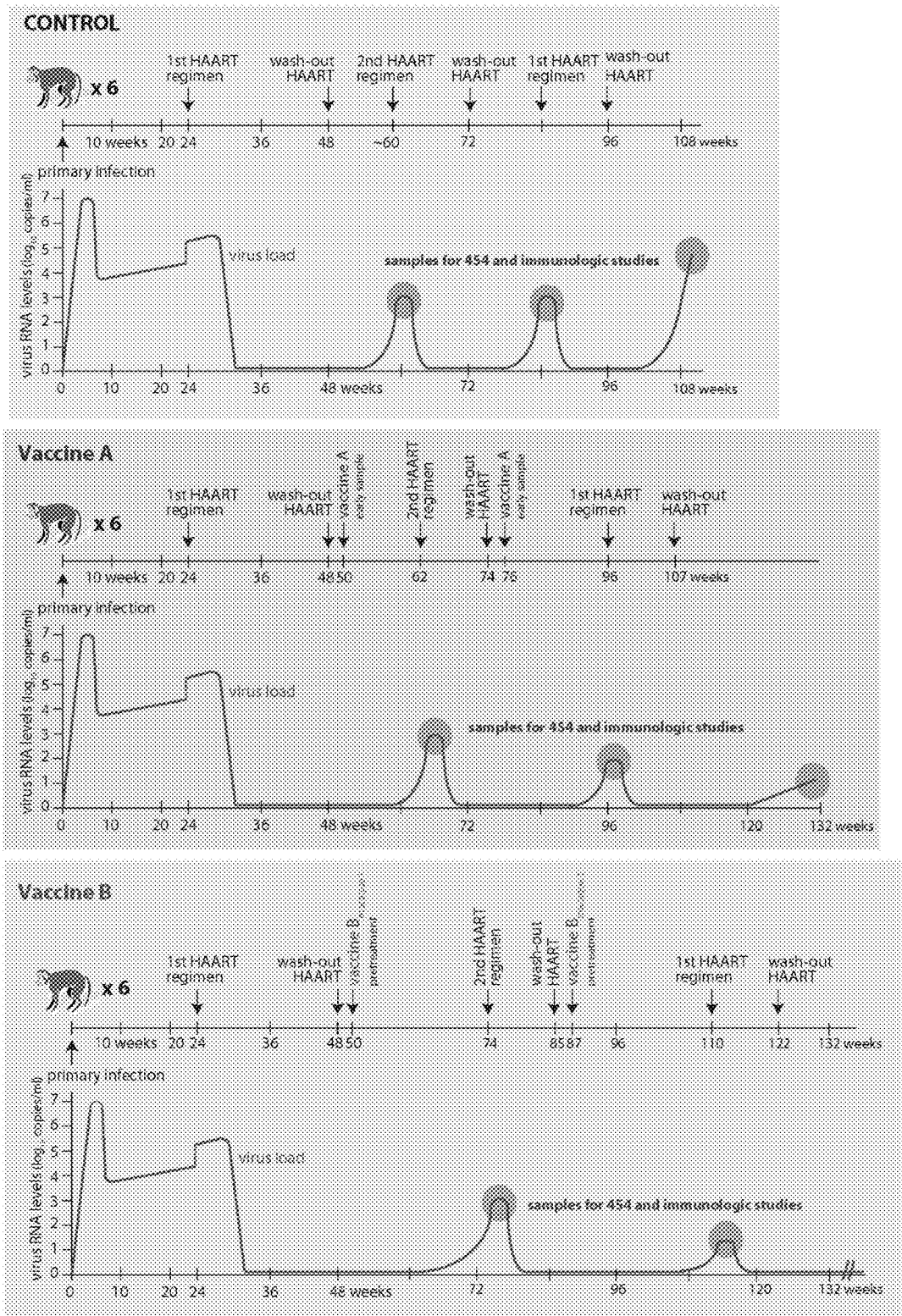

In addition, FIGS. 8 and 9 further illustrate viral rebound after stable HAAART and immunization with autologous vaccine derived from pre-treatment samples and with a vaccine vector based on SIVmac239 versus the control. With removal of combination anti-retroviral treatment or cART (e.g., HAART) concomitant with vaccination, time delays in viral rebound, the SIV genetic diversity of this rebound, and the epitope-specific response in the CD4+ and CD8+ T cell population can be compared. The SIV genetic diversity during virus rebound will be compared to the HIV-1 population found in plasma, PBMCs, resting memory CD4+ T cells of the blood and gut prior to HAART. Macaques will be sacrificed following a second round of vaccinations and HAART to access the remnants of SIV throughout the majority of organs and tissues. It is anticipated that with each vaccination protocol with vaccine B (more so than A), the rebound will reflect the activation of resting memory CD4 T cells that are SIV virus specific. This will in turn stimulate latent virus replication and release (related to rebound). The second vaccination after HAART should result in lower level and delay virus rebound. If eradication is achieved, there should be no viral rebound after stopping the third round of HAART.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A method of reducing latent HIV-specific memory CD4+ T cell pool in a subject, the method comprising:

administering to the subject at least one HIV-1 protein and a pharmaceutically acceptable carrier; and deriving the at least one HIV-1 protein from an autologous infecting HIV-1 virus; wherein the HIV-1 protein stimulates latent HIV-specific memory CD4+ T cells to induce latent HIV-1 replication resulting in HIV-specific memory-CD4+ T cell death in the subject.

2. The method of claim 1, wherein deriving the HIV-1 protein from at least one HIV-1 protein coding sequence comprises the steps of obtaining a biological sample from the subject, preparing the at least one HIV-1 protein coding sequence from the biological sample from the subject, wherein the at least one HIV-1 protein coding sequence includes HIV-1 RNA, and preparing at least one HIV-1 protein coding sequence from a biological sample by reverse transcribing the HIV-1 RNA to produce HIV-1 cDNA and amplifying a fragment of the HIV-1 cDNA, the amplified fragment corresponding to a portion of an HIV-1 protein coding RNA sequence.

3. The method of claim 2, wherein deriving the HIV-1 protein from at least one HIV-1 protein coding sequence comprises the steps of:

introducing the at least one HIV-1 protein coding sequence into at least one expression construct utilizing yeast homologous recombination;

transfecting a cell with the at least one expression construct, wherein the HIV- protein is secreted by the cell; and harvesting the secreted HIV-1 protein.

4. The method of claim 2, wherein the step of deriving the HIV-1 protein from at least one HIV-1 protein coding sequence includes obtaining a blood plasma sample prior to anti-retroviral treatment initiation, the anti-retroviral treatment comprising HAART treatment.

5. The method of claim 3, wherein the HIV-1 protein secreted by the cell is a defective HIV-1 particle including env, gag and pol proteins in the correct stoichometry and is morphologically indistinguishable from a wild type HIV-1.

6. The method of claim 3, wherein the step of introducing the at least one HIV-1 protein coding sequence into at least one expression construct utilizing yeast homologous recombination comprises providing a plasmid expression vector including a near-full length HIV-1 genome having a yeast uracil biosynthesis gene (URA3) in place of a gp120/gp41 HIV-1 envelope protein coding sequence, preparing a gp120/gp41 HIV-1 envelope protein coding sequence from the subject sample, and replacing the yeast uracil biosynthesis gene with the HIV-1 envelope protein coding sequence from the subject sample.

7. The method of claim 6, the HIV-1 envelope protein coding sequence from the subject sample encoding HIV gp120 and an N-terminal portion of gp41.

8. The method of claim 6, wherein the HIV-1 envelope protein coding sequence does not encode a functional portion of the cytoplasmic domain of gp41.

9. The method of claim 3, wherein the step of introducing the at least one HIV-1 protein coding sequence into at least one expression construct utilizing yeast homologous recombination comprises providing a plasmid expression vector including a near-full length HIV-1 genome having a yeast uracil biosynthesis gene (URA3) in place of a HIV-1 gag/pol protein coding sequence, preparing an HIV-1 qaq/pol protein coding sequence from the subject sample, and replacing the yeast uracil biosynthesis gene with an HIV-1 gag/pol protein coding sequence from the subject sample.

10. The method of claim 3, the at least one expression construct comprising a promoter operably linked to the HIV-1 protein coding sequence.

11. The method of claim 3, the at least one expression construct comprising a yeast based plasmid vector.

12. The method of claim 1, further comprising administering one or more anti-viral agents to the subject, the one or more antiviral agents comprising a component of HAART, wherein the component of HAART is selected from a nucleoside reverse transcriptase inhibitor, a non-nucleoside HIV reverse transcriptase inhibitor, and a protease inhibitor.

13. A method of treating latent HIV infection in a subject, the method comprising deriving the at least one HIV-1 protein from an autologous infecting HIV-1 virus; and administering to the subject a therapeutically effective amount of at least one HIV-1 protein and a pharmaceutically acceptable carrier; wherein the therapeutically effective amount of HIV-1 protein stimulates latent HIV-specific memory CD4+ T cells to induce latent HIV-1 replication resulting in HIV-specific memory-CD4+ T cell death in the subject.

14. The method of claim 13, wherein deriving the HIV-1 protein from at least one HIV-1 protein coding sequence comprises the steps of obtaining a biological sample from the subject, preparing the at least one HIV-1 protein coding sequence from the biological sample from the subject, wherein the at least one HIV-1 protein coding sequence includes HIV-1 RNA, and preparing at least one HIV-1 protein coding sequence from a biological sample by reverse transcribing the HIV-1 RNA to produce HIV-1 cDNA and amplifying a fragment of the HIV-1 cDNA, the amplified fragment corresponding to a portion of an HIV-1 protein coding RNA sequence.

15. The method of claim 14, wherein deriving the HIV-1 protein from at least one HIV-1 protein coding sequence comprises the steps of:

introducing the at least one HIV-1 protein coding sequence into at least one expression construct utilizing yeast homologous recombination;

transfecting a cell with the at least one expression construct, wherein the HIV-protein is secreted by the cell; and harvesting the secreted HIV-1 protein.

16. The method of claim 14, wherein the step of deriving the HIV-1 protein from at least one HIV-1 protein coding sequence includes obtaining a blood plasma sample prior to anti-retroviral treatment initiation, the anti-retroviral treatment comprising HAART treatment.

17. The method of claim 15, wherein the HIV-1 protein secreted by the cell is a defective HIV-1 particle including env, gag and pol proteins in the correct stoichometry and is morphologically indistinguishable from a wild type HIV-1.

18. The method of claim 15, wherein the step of introducing the at least one HIV-1 protein coding sequence into at least one expression construct utilizing yeast homologous recombination comprises providing a plasmid expression vector including a near-full length HIV-1 genome having a yeast uracil biosynthesis gene (URA3) in place of a gp120/gp41 HIV-1 envelope protein coding sequence, preparing a gp120/gp41 HIV-1 envelope protein coding sequence from the subject sample, and replacing the yeast uracil biosynthesis gene with an HIV-1 envelope protein coding sequence from the subject sample.

19. The method of claim 18, the HIV-1 envelope protein coding sequence prepared from the subject sample encoding HIV gp120 and an N-terminal portion of gp41.

20. The method of claim 18, wherein the HIV-1 envelope protein coding sequence does not encode a functional portion of the cytoplasmic domain of gp41.

21. The method of claim 15, wherein the step of introducing the at least one HIV-1 protein coding sequence into at least one expression construct utilizing yeast homologous recombination comprises providing a plasmid expression vector including a near-full length HIV-1 genome having a yeast uracil biosynthesis gene (URA3) in place of a HIV-1 gag/pol protein coding sequence, preparing an HIV-1 qaq/pol protein coding sequence from the subject sample, and replacing the yeast uracil biosynthesis gene with an HIV-1 gag/pol protein coding sequence from the subject sample.

22. The method of claim 15, the at least one expression construct comprising a promoter operably linked to the HIV-1 protein coding sequence.

23. The method of claim 15, the at least one expression construct comprising a yeast based plasmid vector.

24. The method of claim 13, further comprising administering a therapeutically effective amount of one or more anti-viral agents to the subject.

25. The method of claim 24, the one or more antiviral agents comprising a component of HAART, wherein the component of HAART is selected from a nucleoside reverse transcriptase inhibitor, a non-nucleoside HIV reverse transcriptase inhibitor, and a protease inhibitor.

26. The method of claim 13, further comprising administering to the subject a therapeutically effective amount of one or more activators of latent HIV expression to the subject.

27. The method of claim 26, the one or more activators of latent HIV expression selected from an HDAC inhibitor or protein kinase C agonist.

* * * * *

SEQUENCE LISTING

```
<160> NUMBER OF SEQ ID NOS: 12

<210> SEQ ID NO 1
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (33)..(33)
<223> OTHER INFORMATION: R=A+G
<220> FEATURE:
<221> NAME/KEY: misc_feature
<222> LOCATION: (37)..(37)
<223> OTHER INFORMATION: Y=C+T
<220> FEATURE:
<221> NAME/KEY: misc_feature
<222> LOCATION: (38)..(38)
<223> OTHER INFORMATION: R=A+G
<220> FEATURE:
<221> NAME/KEY: misc_feature
<222> LOCATION: (39)..(39)
```

```
<223> OTHER INFORMATION: N=A+C+G+T
<220> FEATURE:
<221> NAME/KEY: misc_feature
<222> LOCATION: (44)..(45)
<223> OTHER INFORMATION: H=A+T+C
<220> FEATURE:
<221> NAME/KEY: misc_feature
<222> LOCATION: (49)..(49)
<223> OTHER INFORMATION: Y=C+T
<220> FEATURE:
<221> NAME/KEY: misc_feature
<222> LOCATION: (50)..(50)
<223> OTHER INFORMATION: M=A+C

<400> SEQUENCE: 1
aacctataat agtagcaata gtagcattag tartagyrnt aathhtagym                 50

<210> SEQ ID NO 2
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (31)..(32)
<223> OTHER INFORMATION: N=A+C+G+T
<220> FEATURE:
<221> NAME/KEY: misc_feature
<222> LOCATION: (35)..(35)
<223> OTHER INFORMATION: Y=C+T
<220> FEATURE:
<221> NAME/KEY: misc_feature
<222> LOCATION: (38)..(38)
<223> OTHER INFORMATION: Y=C+T
<220> FEATURE:
<221> NAME/KEY: misc_feature
<222> LOCATION: (39)..(39)
<223> OTHER INFORMATION: M=A+C
<220> FEATURE:
<221> NAME/KEY: misc_feature
<222> LOCATION: (41)..(41)
<223> OTHER INFORMATION: R=A+G
<220> FEATURE:
<221> NAME/KEY: misc_feature
<222> LOCATION: (47)..(47)
<223> OTHER INFORMATION: H=A+T+C
<220> FEATURE:
<221> NAME/KEY: misc_feature
<222> LOCATION: (48)..(48)
<223> OTHER INFORMATION: R=A+G

<400> SEQUENCE: 2
tgctgtttat ccatttcaga attgggtgtc nncayagymg ratagghrtt                 50

<210> SEQ ID NO 3
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (31)..(31)
<223> OTHER INFORMATION: R=A+G
<220> FEATURE:
<221> NAME/KEY: misc_feature
<222> LOCATION: (34)..(34)
<223> OTHER INFORMATION: Y=C+T
<220> FEATURE:
<221> NAME/KEY: misc_feature
<222> LOCATION: (35)..(35)
<223> OTHER INFORMATION: R=A+G
<220> FEATURE:
<221> NAME/KEY: misc_feature
```

```
<222> LOCATION: (36)..(37)
<223> OTHER INFORMATION: Y=C+T
<220> FEATURE:
<221> NAME/KEY: misc_feature
<222> LOCATION: (42)..(42)
<223> OTHER INFORMATION: W=A+T
<220> FEATURE:
<221> NAME/KEY: misc_feature
<222> LOCATION: (43)..(43)
<223> OTHER INFORMATION: Y=C+T
<220> FEATURE:
<221> NAME/KEY: misc_feature
<222> LOCATION: (46)..(46)
<223> OTHER INFORMATION: R=A+G
<220> FEATURE:
<221> NAME/KEY: misc_feature
<222> LOCATION: (49)..(49)
<223> OTHER INFORMATION: Y=C+T
<220> FEATURE:
<221> NAME/KEY: misc_feature
<222> LOCATION: (50)..(50)
<223> OTHER INFORMATION: R=A+G

<400> SEQUENCE: 3
agccataata agaattctgc aacaactgct rttyryycat twyagratyr        50

<210> SEQ ID NO 4
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (34)..(34)
<223> OTHER INFORMATION: Y=C+T
<220> FEATURE:
<221> NAME/KEY: misc_feature
<222> LOCATION: (35)..(35)
<223> OTHER INFORMATION: N=A+C+G+T
<220> FEATURE:
<221> NAME/KEY: misc_feature
<222> LOCATION: (36)..(36)
<223> OTHER INFORMATION: K=T+G
<220> FEATURE:
<221> NAME/KEY: misc_feature
<222> LOCATION: (41)..(41)
<223> OTHER INFORMATION: R=A+G
<220> FEATURE:
<221> NAME/KEY: misc_feature
<222> LOCATION: (44)..(44)
<223> OTHER INFORMATION: D=A+T+G
<220> FEATURE:
<221> NAME/KEY: misc_feature
<222> LOCATION: (45)..(45)
<223> OTHER INFORMATION: H=A+T+C
<220> FEATURE:
<221> NAME/KEY: misc_feature
<222> LOCATION: (47)..(47)
<223> OTHER INFORMATION: R=A+G
<220> FEATURE:
<221> NAME/KEY: misc_feature
<222> LOCATION: (48)..(48)
<223> OTHER INFORMATION: Y=C+T
<220> FEATURE:
<221> NAME/KEY: misc_feature
<222> LOCATION: (50)..(50)
<223> OTHER INFORMATION: D=A+T+G

<400> SEQUENCE: 4
atacttgggc aggagtggaa gccataataa gaaynktgca rcadhtrytd        50

<210> SEQ ID NO 5
<211> LENGTH: 50
<212> TYPE: DNA
```

```
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (32)..(32)
<223> OTHER INFORMATION: Y=C+T
<220> FEATURE:
<221> NAME/KEY: misc_feature
<222> LOCATION: (33)..(33)
<223> OTHER INFORMATION: K=T+G
<220> FEATURE:
<221> NAME/KEY: misc_feature
<222> LOCATION: (33)..(33)
<223> OTHER INFORMATION: K=T+G
<220> FEATURE:
<221> NAME/KEY: misc_feature
<222> LOCATION: (37)..(37)
<223> OTHER INFORMATION: K=T+G
<220> FEATURE:
<221> NAME/KEY: misc_feature
<222> LOCATION: (41)..(41)
<223> OTHER INFORMATION: Y=C+T
<220> FEATURE:
<221> NAME/KEY: misc_feature
<222> LOCATION: (44)..(44)
<223> OTHER INFORMATION: Y=C+T
<220> FEATURE:
<221> NAME/KEY: misc_feature
<222> LOCATION: (49)..(49)
<223> OTHER INFORMATION: K=T+G

<400> SEQUENCE: 5
gttcactaat cgaatggatc tgtctctgtc tykctckcca yctycttckt         50

<210> SEQ ID NO 6
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (33)..(33)
<223> OTHER INFORMATION: Y=C+T
<220> FEATURE:
<221> NAME/KEY: misc_feature
<222> LOCATION: (36)..(36)
<223> OTHER INFORMATION: Y=C+T
<220> FEATURE:
<221> NAME/KEY: misc_feature
<222> LOCATION: (37)..(37)
<223> OTHER INFORMATION: K=T+G
<220> FEATURE:
<221> NAME/KEY: misc_feature
<222> LOCATION: (41)..(41)
<223> OTHER INFORMATION: K=T+G
<220> FEATURE:
<221> NAME/KEY: misc_feature
<222> LOCATION: (45)..(45)
<223> OTHER INFORMATION: Y=C+T
<220> FEATURE:
<221> NAME/KEY: misc_feature
<222> LOCATION: (48)..(48)
<223> OTHER INFORMATION: Y=C+T

<400> SEQUENCE: 6
atccgttcac taatcgaatg gatctgtctc tgyctykctc kccayctyct         50

<210> SEQ ID NO 7
<211> LENGTH: 50
<212> TYPE: DNA
<213> ORGANISM: Artificial Sequence
<220> FEATURE:
<223> OTHER INFORMATION: Oligonucleotide - HIV-1
```

<220> FEATURE:
<221> NAME/KEY: misc_feature
<222> LOCATION: (37)..(37)
<223> OTHER INFORMATION: B=T+C+G
<220> FEATURE:
<221> NAME/KEY: misc_feature
<222> LOCATION: (38)..(38)
<223> OTHER INFORMATION: Y=C+T
<220> FEATURE:
<221> NAME/KEY: misc_feature
<222> LOCATION: (40)..(40)
<223> OTHER INFORMATION: Y=C+T
<220> FEATURE:
<221> NAME/KEY: misc_feature
<222> LOCATION: (43)..(43)
<223> OTHER INFORMATION: Y=C+T
<220> FEATURE:
<221> NAME/KEY: misc_feature
<222> LOCATION: (46)..(46)
<223> OTHER INFORMATION: Y=C+T
<220> FEATURE:
<221> NAME/KEY: misc_feature
<222> LOCATION: (47)..(47)
<223> OTHER INFORMATION: K=T+G

<400> SEQUENCE: 7
agtgctaagg atccgttcac taatcgaatg gatctgbyty tgyctykctc                50

<210> SEQ ID NO 8
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (32)..(32)
<223> OTHER INFORMATION: R=A+G
<220> FEATURE:
<221> NAME/KEY: misc_feature
<222> LOCATION: (34)..(34)
<223> OTHER INFORMATION: H=A+T+C
<220> FEATURE:
<221> NAME/KEY: misc_feature
<222> LOCATION: (39)..(39)
<223> OTHER INFORMATION: M=A+C
<220> FEATURE:
<221> NAME/KEY: misc_feature
<222> LOCATION: (41)..(41)
<223> OTHER INFORMATION: R=A+G
<220> FEATURE:
<221> NAME/KEY: misc_feature
<222> LOCATION: (49)..(49)
<223> OTHER INFORMATION: Y=C+T

<400> SEQUENCE: 8
catattagga cgtatagtta gtcctaggtg trahtatcma rcaggacaya                50

<210> SEQ ID NO 9
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (31)..(31)
<223> OTHER INFORMATION: H=A+T+C
<220> FEATURE:
<221> NAME/KEY: misc_feature
<222> LOCATION: (39)..(39)
<223> OTHER INFORMATION: R=A+G
<220> FEATURE:
<221> NAME/KEY: misc_feature
<222> LOCATION: (40)..(41)

<223> OTHER INFORMATION: Y=C+T
<220> FEATURE:
<221> NAME/KEY: misc_feature
<222> LOCATION: (44)..(44)
<223> OTHER INFORMATION: R=A+G
<220> FEATURE:
<221> NAME/KEY: misc_feature
<222> LOCATION: (50)..(50)
<223> OTHER INFORMATION: Y=C+T

<400> SEQUENCE: 9
ggcgaatagc tctataagct gcttgtaata httctatary yctrtctgty                 50

<210> SEQ ID NO 10
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (32)..(32)
<223> OTHER INFORMATION: Y=C+T
<220> FEATURE:
<221> NAME/KEY: misc_feature
<222> LOCATION: (33)..(33)
<223> OTHER INFORMATION: R=A+G
<220> FEATURE:
<221> NAME/KEY: misc_feature
<222> LOCATION: (40)..(40)
<223> OTHER INFORMATION: N=A+C+G+T
<220> FEATURE:
<221> NAME/KEY: misc_feature
<222> LOCATION: (42)..(42)
<223> OTHER INFORMATION: Y=C+T
<220> FEATURE:
<221> NAME/KEY: misc_feature
<222> LOCATION: (45)..(45)
<223> OTHER INFORMATION: Y=C+T
<220> FEATURE:
<221> NAME/KEY: misc_feature
<222> LOCATION: (48)..(48)
<223> OTHER INFORMATION: Y=C+T

<400> SEQUENCE: 10
actgctatgg ctgtggcatt gagcaagtta ayrgcactan tyttyagytc                 50

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide - HIV-1

<400> SEQUENCE: 11
ccaggagcga cactagaaga                                                  20

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide - HIV-1

<400> SEQUENCE: 12
gacaggttaa ttgatagact                                                  20